(12) United States Patent
Chen

(10) Patent No.: US 10,745,444 B2
(45) Date of Patent: Aug. 18, 2020

(54) CYCLOPEPTIDE, PHARMACEUTICAL OR COSMETIC COMPOSITION COMPRISING THE SAME AND METHOD FOR PREPARING THE SAME

(71) Applicant: National Tsing Hua University, Hsinchu (TW)

(72) Inventor: Chien-Tien Chen, Hsinchu County (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 0 days.

(21) Appl. No.: 15/488,550

(22) Filed: Apr. 17, 2017

(65) Prior Publication Data

US 2018/0298060 A1   Oct. 18, 2018

(51) Int. Cl.
| | | |
|---|---|---|
| *C07K 7/64* | (2006.01) | |
| *A61K 8/64* | (2006.01) | |
| *A61Q 19/08* | (2006.01) | |
| *A61K 38/00* | (2006.01) | |

(52) U.S. Cl.
CPC .............. *C07K 7/64* (2013.01); *A61K 8/64* (2013.01); *A61Q 19/08* (2013.01); *A61K 38/00* (2013.01)

(58) Field of Classification Search
None
See application file for complete search history.

(56) References Cited

U.S. PATENT DOCUMENTS

| | | | | |
|---|---|---|---|---|
| 6,127,335 A * | 10/2000 | Jonczyk | ........... | C07K 7/64 514/1.3 |
| 9,481,712 B2 * | 11/2016 | Afonin | ........... | C07K 7/06 |
| 10,494,403 B2 * | 12/2019 | Chen | ........... | A61K 8/64 |
| 2011/0027209 A1 * | 2/2011 | Anzali | ........... | A61K 8/64 424/70.1 |

FOREIGN PATENT DOCUMENTS

| | | |
|---|---|---|
| CN | 1218478 A | 6/1999 |
| DE | 19613933 A1 | 10/1997 |
| WO | 2009124754 A1 | 10/2009 |

OTHER PUBLICATIONS

Bianchini et al. (125I-Radiolabeled Morpholine-Containing Arginine—Glycine—Aspartate (RGD) Ligand of αvβ3 Integrin As a Molecular Imaging Probe for Angiogenesis. J. Med. Chem., 2012, 55 (11), pp. 5024-5033).*
Graf et al., "In Vivo Anti-Aging Efficacy of a Cyclic Peptide Composition", IFSCC Magazine Jan. 2012, pp. 23-27.
Denardo et al., "Neovascular Targeting with Cyclic RGD Peptide (cRGDf-ACHA) to Enhance Delivery of Radioimmunotherapy", Cancer Biotherapy & Radiopharmaceuticals, vol. 15, No. 1, 2000, pp. 71-79.
Translation of Office Action in corresponding Taiwanese Application 107107206, dated Jan. 16, 2019.
Translation of response to TW Office Action in corresponding Taiwanese Application 107107206, dated Feb. 26, 2019.
Citation 1—Graf et al., "In Vivo Anti-Aging Efficacy of a Cyclic Peptide Composition", IFSCC Magazine Jan. 2012, pp. 23-27.
Citation 2—Denardo et al., "Neovascular Targeting with Cyclic RGD Peptide (cRGDf-ACHA) to Enhance Delivery of Radioimmunotherapy", Cancer Biotherapy & Radiopharmaceuticals, vol. 15, No. 1, 2000, pp. 71-79.
Translation of corresponding Taiwanese application 107107206.
Translation of corresponding Taiwanese publication of TW application 107107206.

* cited by examiner

*Primary Examiner* — Maury A Audet
(74) *Attorney, Agent, or Firm* — Bacon & Thomas, PLLC

(57) ABSTRACT

A cyclopeptide is disclosed, which is represented by the following formula (I) or (I'):

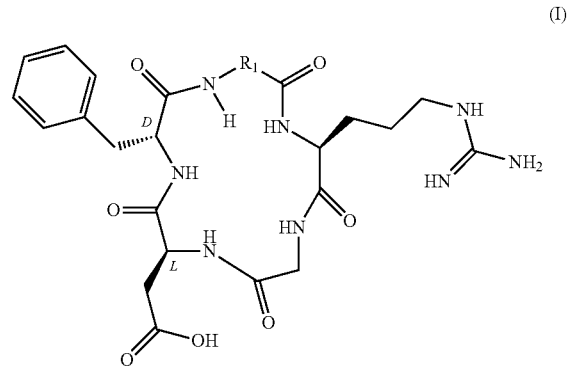

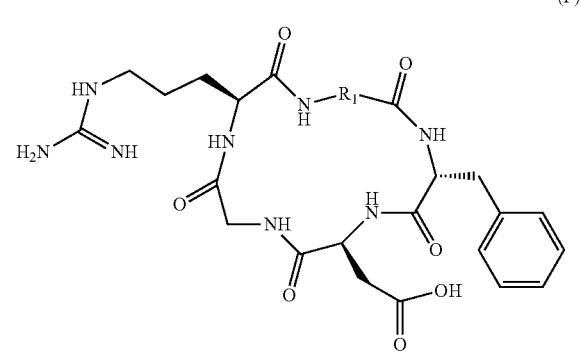

wherein $R_1$ is defined in the specification. In addition, a pharmaceutical or cosmetic composition comprising the same and a method for preparing the same are also disclosed.

3 Claims, No Drawings

CYCLOPEPTIDE, PHARMACEUTICAL OR COSMETIC COMPOSITION COMPRISING THE SAME AND METHOD FOR PREPARING THE SAME

BACKGROUND OF THE INVENTION

1. Field of the Invention

The present invention relates to a cyclopeptide, a pharmaceutical or cosmetic composition comprising the same and a method for preparing the same. More specifically, the present invention relates to a topical or cosmetic skin care cyclopeptide, a pharmaceutical or cosmetic composition comprising the same and a method for preparing the same.

2. Description of Related Art

Peptides have found widespread use in various fields, for example, topical or cosmetic skin care uses. Among the known peptides, the peptide with arginine (R)-glycine (G)-aspartate (D) motif is found as a common element in cellular recognition.

It is known that the peptide containing RGD motif can bind to the intergrin RGD binding site, and can be used to coat synthetic scaffolds in tissue engineering to enhance cellular attachment by mimicking in vivo conditions.

In the conventional method for preparing the peptide containing RGD motif, coupling agents have to be used to catalyze the peptide synthesis. However, the used amount of the coupling agents is not less, and the cost of the coupling agents itself is high. Hence, the production cost of the peptide is not low, and the obtained peptide cannot be available to all.

Therefore, it is desirable to provide a novel peptide containing RGD motif and a novel method for preparing the peptide; so, the obtained peptide can be widely applied to various fields.

SUMMARY OF THE INVENTION

The object of the present invention is to provide a novel cyclopeptide and a pharmaceutical or cosmetic composition comprising the same.

The RGD- and GRD-cyclopeptides of the present invention are respectively represented by the following formula (I) and (I'):

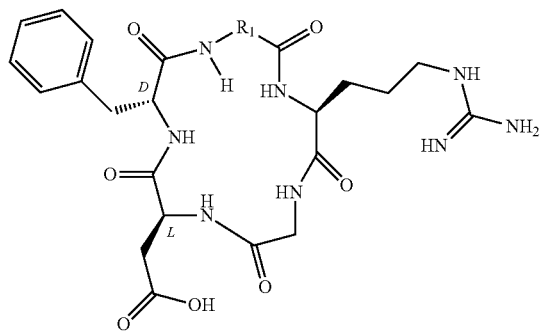

(I)

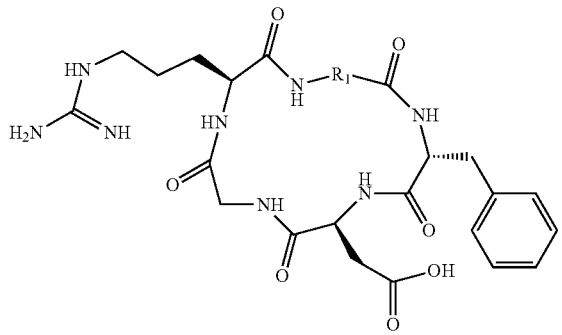

(I')

wherein, $R_1$ is

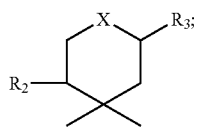

each of $R_2$ and $R_3$ independently is H or $C_{1-6}$ alkyl;
X is O, S, $CH_2$ or N—$R_4$, in which $R_4$ is H, $C_{1-6}$ alkyl, $(CH_2CH_2O)_nH$—C(=O)—$C_{1-10}$ alkyl, or C(=O)($C_2H_4$)C(=O)O($C_2H_4O$)$_n$H, in which n=1-3.

Preferably, in the cyclopeptide of the present invention, $R_3$ is $C_{1-6}$ alkyl when X is $CH_2$.

The pharmaceutical or cosmetic composition of the present invention comprises: an excipient; and the aforementioned cyclopeptide of the present invention.

In the cyclopeptide and the pharmaceutical or cosmetic composition of the present invention, X preferably is O, $CH_2$ or N—$R_4$, in which $R_4$ is H, $C_{1-6}$ alkyl, —C(=O)—$C_{4-10}$ alkyl, $(CH_2CH_2O)_nH$, or C(=O)($C_2H_4$)$_2$C(=O)O($C_2H_4O$)$_n$H, in which n=1-3.

In the cyclopeptide and the pharmaceutical or cosmetic composition of the present invention, $R_1$ preferably is

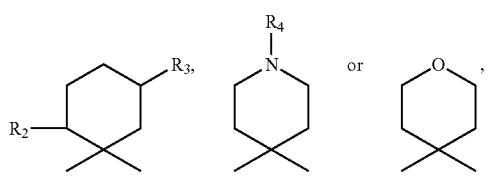

in which $R_2$ is H or $C_{1-6}$ alkyl, $R_3$ is $C_{1-6}$ alkyl; and $R_4$ is H, —C(=O)—$C_{4-10}$ alkyl or $(CH_2CH_2O)_nH$. More preferably, $R_2$ is i-propyl, $R_3$ is methyl when $R_1$ is

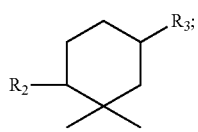

or R₄ is H or —C(=O)-heptyl when R₁ is
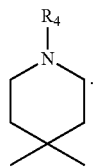
In one preferred aspect of the present invention, the cyclopeptides of the present invention are represented by any one of the following formulas (I-1) to (I-5) and (I'-1) to (I'-5):
(I-1)
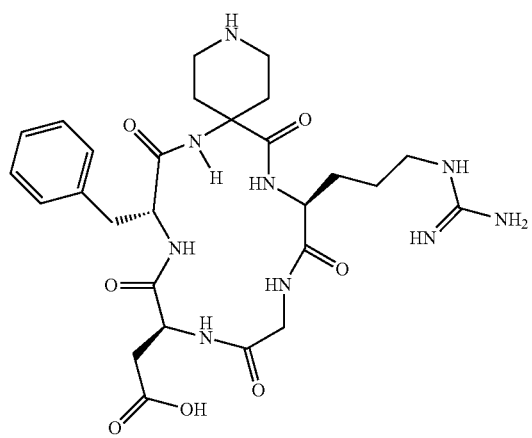
(I-2)
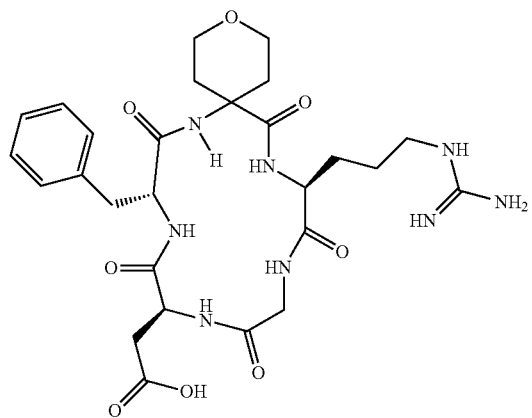
(I-3)
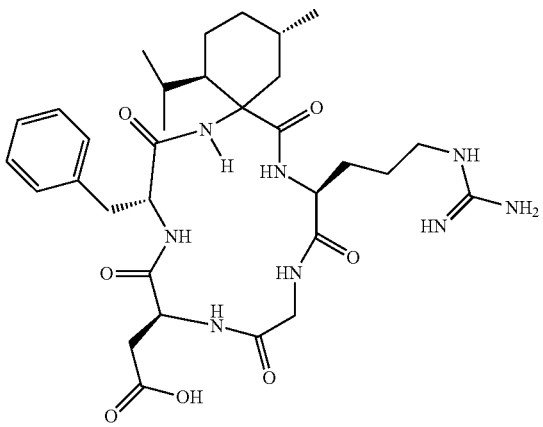
(I-4)
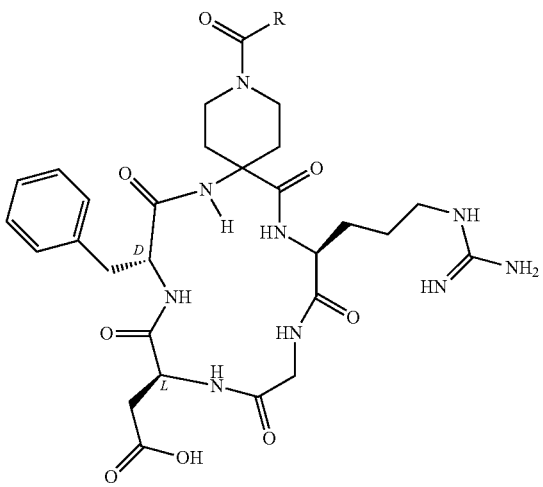
(I-5)
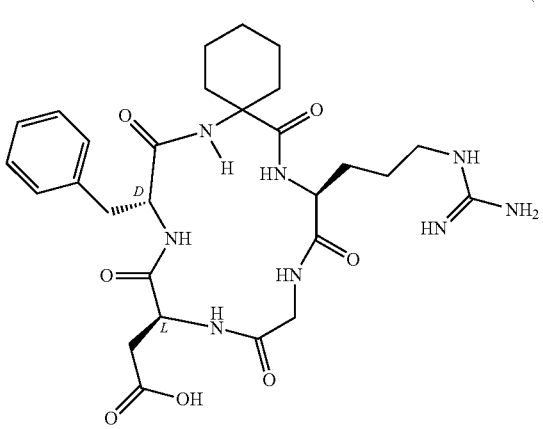

-continued (I'-1)
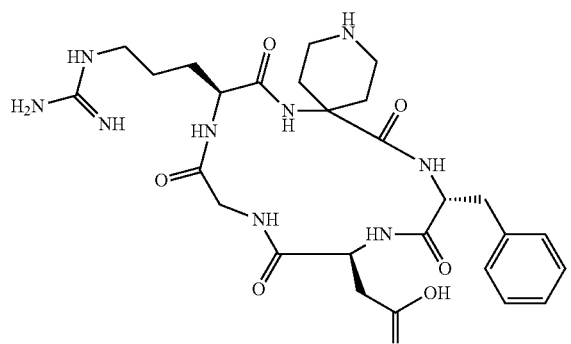

(I'-2)
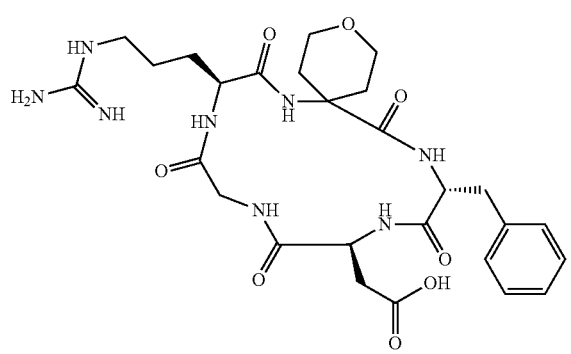

(I'-3)
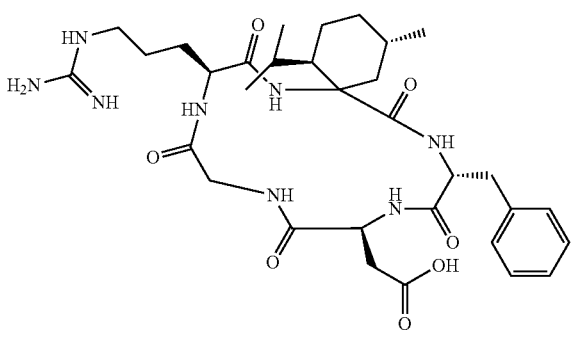

(I'-4)
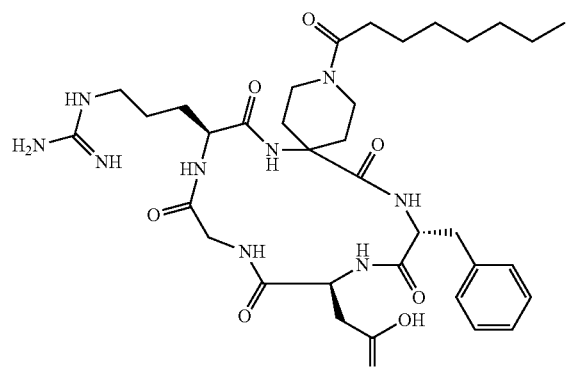

-continued (I'-5)
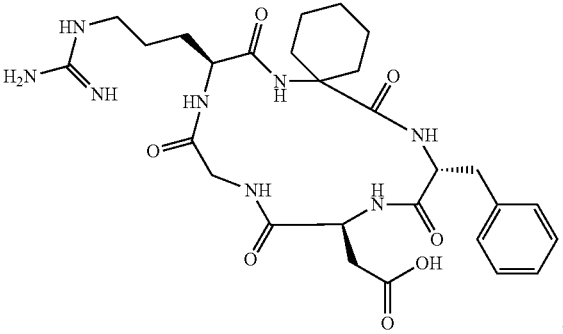

The cyclopeptide of the present invention comprises amino acids of arginine (R), glycine (G) and aspartate (D), which can bind to the intergrin RGD binding site. When the cyclopeptide of the present invention binds to the intergrin RGD binding site of the skin, the communication process between dermis and epidermis can be revived, and the production of important proteins of the basement membrane can be stimulated. Therefore, the purpose of ameliorating scars, wounds, inflammatory processes, aging and/or wrinkle formation can be achieved. Hence, the cyclopeptide and the pharmaceutical or cosmetic composition of the present invention can be applied to topical or cosmetic skin care composition.

Preferably, in the cyclopeptide of the present invention, the cyclopeptide of the present invention is represented by any one of the compounds of formulas (I-1) to (I-5) and (I'-1) to (I'-5). The product of the compound of formula (I'-5) after metabolism is ACHA (aminocyclohexane carboxylic acid) derivative, which is a non-natural amino acid. However, for example, the product of the compound of formula (I'-3) is menthone, which is a natural molecule. Hence, compared to compound of formula (I'-5), the compound of formulas (I'-1) to (I'-4) is preferable.

In the pharmaceutical or cosmetic composition of the present invention, the suitable excipient for the present invention can be any excipient used in the art, for example, a binder, an anti-adhesive agent, a dispersant and a lubricant.

Except for the aforementioned cyclopeptide and pharmaceutical or cosmetic composition of the present invention, another object of the present invention is to provide a novel bio-compatible, catalytic method for preparing the cyclopeptide of the present invention.

The method of the present invention comprises the following steps (A) to (D).

In the step (A), compounds represented by the following formulas (II-1) or (II'-1), and (II-2) are provided from commercial source or made by our catalytic methods.

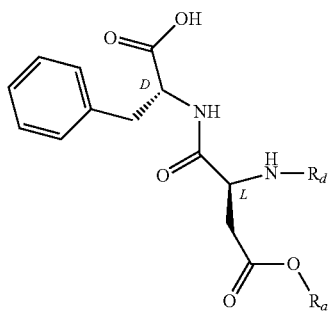 (II-1)

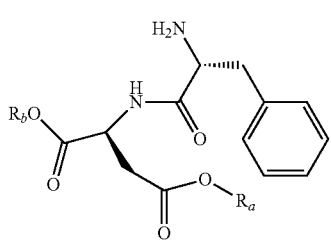 (II'-1)

$R_c$—NH—$R_1$—COOH (II-2)

Herein, each of $R_a$, and $R_b$ independently is alkyl, cycloalkyl, aryl or heteroaryl;
$R_c$ is a protection group; and
$R_1$ is

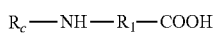

in which each of $R_2$ and $R_3$ independently is H or $C_{1-6}$ alkyl; X is O, S, $CH_2$ or N—$R_4$, in which $R_4$ is H, $C_{1-6}$ alkyl, $(CH_2CH_2O)_nH$, —C(=O)—$C_{1-10}$ alkyl, or C(=O)$(C_2H_4)_2C(=O)O(C_2H_4O)_nH$, in which n=1-3.

In the step (B), a reaction between the compounds of formulas (II-1) or (II'-1) and (II-2) is performed to obtain a compound represented by the following formula (II-3) and (II'-3), respectively,

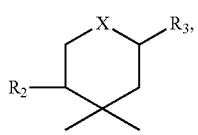 (II-3)

and

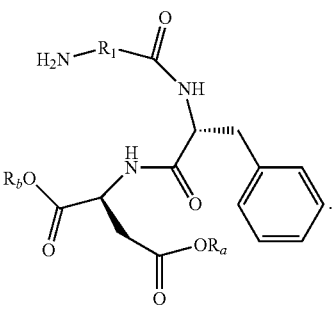 (II'-3)

In the step (C), a reaction between the compound of formula (II-3) or (II'-3) and a compound represented by the following formula (II-4) or (II'-4), respectively, is performed to obtain a compound represented by the following formula (II-5) and (II'-5), respectively.

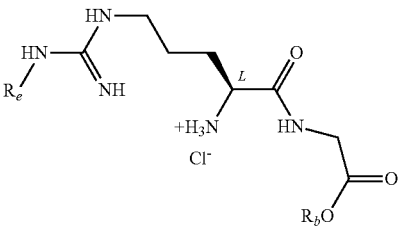 (II-4)

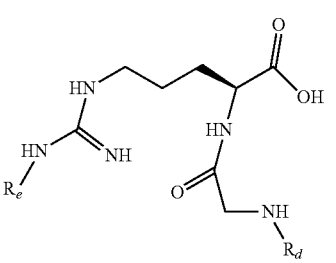 (II'-4)

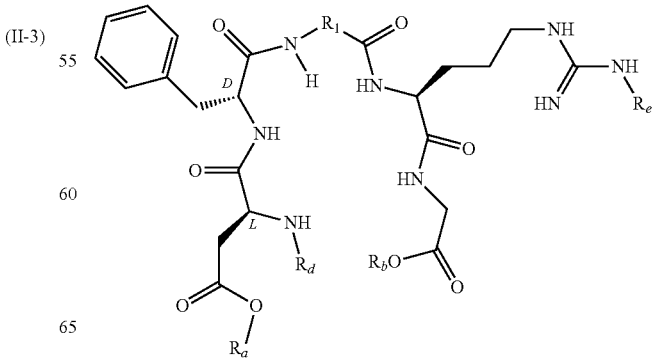 (II-5)

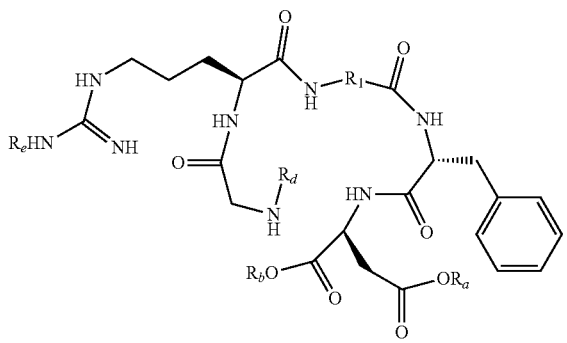

wherein, each of $R_d$ and $R_e$, independently is a protection group.

In the step (D), a cyclization reaction of the compound of formula (II-5) or (II'-5) is performed with a catalyst of formula (III), to obtain a compound represented by the formula (I) or (I'), respectively.

wherein M is a metal selected from the group consisting of IVB, VB, VIB and actinide groups;
$L^1$ and $L^2$ respectively is a ligand;
m and y are integers of greater than or equal to 1; and
z is an integer of greater than or equal to zero.

In the method of the present invention, $R_c$ and $R_d$ can be Fluorenylmethyloxycarbonyl (Fmoc); and $R_e$ can be MTr (4-methoxy-2,3,6-trimethylbenzenesulphonyl). However, the present invention is not limited thereto.

In the method of the present invention, the reaction between the compounds of formulas (II-1) or (II'-1) and (II-2) or the reaction between the compound of formula (II-3) and (II-4) or (II'-3) and (II'-4) can be performed with the catalyst of formula (III) or a coupling agent.

In the method of the present invention, when the reactions in the steps (B) to (D) are performed with the catalyst of formula (III), the catalyst used in the steps (B) to (D) can be the same or different.

In the catalyst of formula (III), $L^1$ is a ligand, which preferably is selected from the group consisting of Cl, OTf, OTs, NTf$_2$, halogen, RC(O)CHC(O)R, OAc, OC(O)CF$_3$, OEt, O—Pr, and butyl, in which R is alkyl (preferably, $C_{1-6}$ alkyl; more preferably, $C_{1-3}$ alkyl). In addition, $L^2$ is also a ligand, which preferably is selected from the group consisting of Cl, H$_2$O, CH$_3$OH, EtOH, THF, CH$_3$CN and

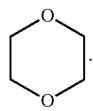

Furthermore, in the catalyst of formula (III), M can be a metal selected from the group consisting of IVB, VB, VIB and actinide groups. In one aspect, M is a group IVB transition element, m is 1 and y is 2; wherein M can be Ti, Zr of Hf. In another aspect, M is a group VB transition element, m is 1 and y is 2 or 3; wherein M can be V or Nb. In another aspect, M is a group VIB transition element, m is 1 and y is 4; wherein M is Mo, W or Cr. In another aspect, M is a group VIB transition element, m is 2 and y is 2; wherein M is Mo, W or Cr. In further another aspect, M is selected from the actinide group, m is 2 and y is 2; wherein M is U. Specific examples for the catalyst of formula (III) can be MoO$_2$Cl$_2$, V(O)OCl$_2$, V(O)(OAc)$_2$, V(O)(O$_2$CCF$_3$)$_2$, Ti(O)(acac)$_2$, Zr(O)Cl$_2$, Hf(O)Cl$_2$, Nb(O)Cl$_2$, MoO$_2$(acac)$_2$, V(O)(OTs)$_2$, V(O)(NTf$_2$)$_2$, or VO(OTf)$_2$, but the present invention is not limited thereto.

Furthermore, in the catalyst of formula (III), z can be an integer of greater than or equal to zero; and preferably, z is 0.

In the conventional method for preparing the cyclopeptide, 3-5 equivalent of coupling agents such as Hydroxybenzotriazole (HOBt), 1-Hydroxy-7-azabenzotriazole (HOAt), 2-(1H-benzotriazol-1-yl)-1,1,3,3-tetramethyluronium hexafluorophosphate (HBTU) and benzotriazol-1-yl-oxytripyrrolidinophosphonium hexafluorophosphate (PyBOP) are used. Because these coupling agents are expensive, the obtained cyclopeptide cannot be easily commercialized and applied to various fields.

In the method for preparing the cyclopeptide of the present invention, the catalyst of formula (III) is water soluble and used to facilitate the reaction progress. Hence, the expensive coupling agents are not used in the method of the present invention. Therefore, cyclopeptide can be produced in a cheaper manner, and the obtained cyclopeptide can be applied to various fields.

In the present invention, alkyl, cycloalkyl, aryl, and heteroaryl present in the compounds include both substituted and unsubstituted moieties, unless specified otherwise. Possible substituents on alkyl, cycloalkyl, aryl, and heteroaryl include, but are not limited to, alkyl, alkenyl, halogen, alkoxy, ketone, alcohol, thioether, carbamate, amino, heterocyclic group or aryl; but alkyl cannot be substituted with alkyl.

In the present invention, the term "halogen" includes F, Cl, Br and I; and preferably is Cl or I. The term "alkyl" refers to linear and branched alkyl; preferably, includes linear and branched $C_{1-20}$ alkyl; more preferably, includes linear and branched $C_{1-12}$ alkyl; and most preferably, includes linear and branched $C_{1-6}$ alkyl. Specific examples of alkyl include, but are not limited to, methyl, ethyl, n-propyl, iso-propyl, n-butyl, sec-butyl, iso-butyl, tert-butyl, pentyl, neo-pentyl or hexyl. The term "alkoxy" refers to a moiety that the alkyl defined in the present invention coupled with an oxygen atom; preferably, includes linear and branched $C_{1-20}$ alkoxy; more preferably, includes linear and branched $C_{1-12}$ alkoxy; and most preferably, includes linear and branched $C_{1-6}$ alkoxy. Specific examples of alkoxy include, but are not limited to, methoxy, ethoxy, n-propoxy, iso-propoxy, n-butoxy, iso-butoxy, sec-butoxy, tert-butoxy, pentyloxy, neo-pentyloxy or hexyloxy. The term "alkenyl" refers to a linear or branched hydrocarbon moiety that contains at least one double bond; preferably, includes a linear and branched hydrocarbon $C_{2-20}$ moiety containing at least one double bond; more preferably, includes a linear and branched hydrocarbon $C_{2-12}$ moiety containing at least one double bond; and most preferably, includes a linear and branched hydrocarbon $C_{2-6}$ moiety containing at least one double bond. Specific examples of alkenyl include, but are not limited to, ethenyl, propenyl, allyl, or 1,4-butadienyl. The term "aryl" refers to a monovalent 6-carbon monocyclic, 10-carbon bicyclic, or 14-carbon tricyclic aromatic ring system. Specific examples of aryl include, but are not limited to, phenyl, naphthyl, pyrenyl, anthracenyl or phenanthryl; and preferably, the aryl is phenyl. The term "heterocyclic group" refers to a 5-8 membered monocyclic, 8-12 membered bicyclic or 11-14 membered tricyclic heteroaryl or heterocycloalkyl having at least one heteroatom which is selected from the group consisting of O, S and N. Specific examples of heterocyclic group include, but are not limited to, pyridyl, pyrimidinyl, furyl, thiazolyl, imidazolyl or thienyl.

Other objects, advantages, and novel features of the invention will become more apparent from the following detailed description when taken in conjunction with the accompanying drawings.

DETAILED DESCRIPTION OF THE PREFERRED EMBODIMENT

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

The cyclopeptide of one preferred embodiment of the present invention can be prepared as follows.

[Scheme I]

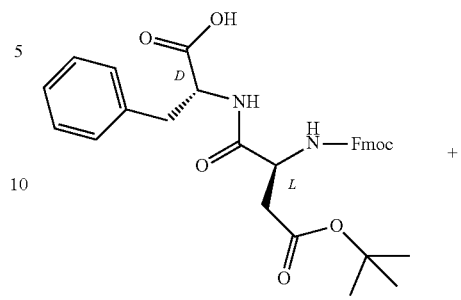

+

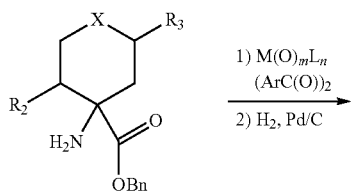

[Scheme I']

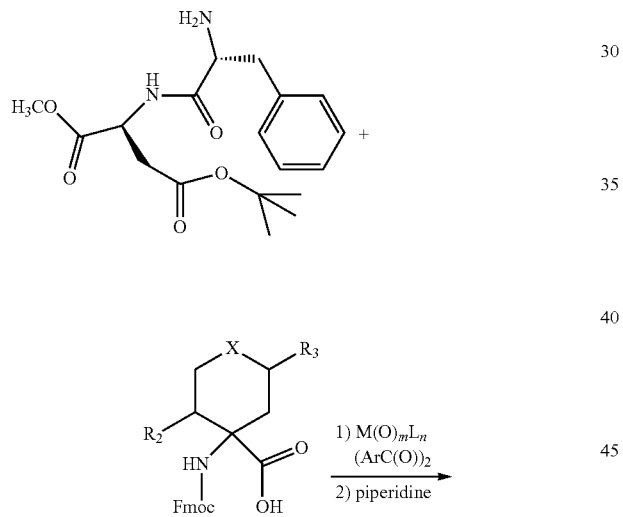

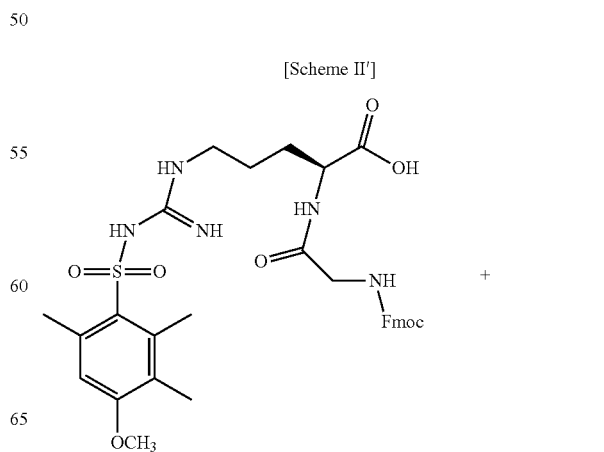

[Scheme II']

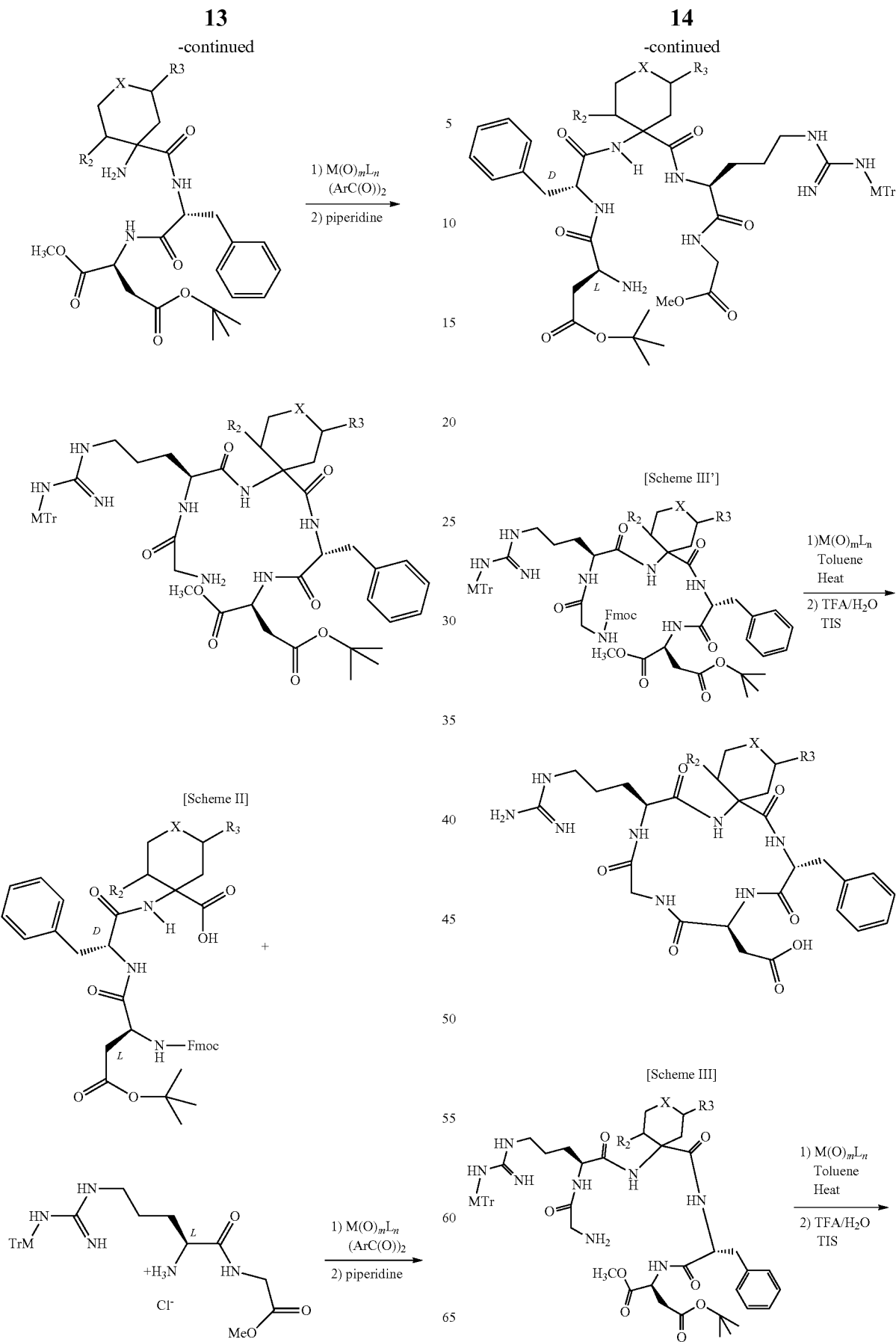

-continued

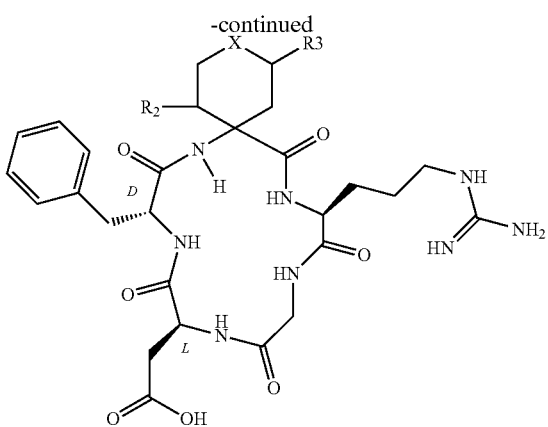

In Scheme I' and II', the coupling agents may also be used and can be, for example, Hydroxybenzotriazole (HOBt), 1-Hydroxy-7-azabenzotriazole (HOAt), 2-(1H-benzotriazol-1-yl)-1,1,3,3-tetramethyluronium hexafluorophosphate (HBTU) and benzotriazol-1-yl-oxytripyrrolidinophosphonium hexafluorophosphate (PyBOP).

Hereinafter, the present invention provides examples for preparing the cyclopeptide of the present invention; but the present is not limited thereto.

1-Amino-cis-4-methylcyclohexanecarboxylic Acid

4-Methylcyclohexanone (45 g., 0.4 mole), potassium cyanide (30 g., 0.4 mole), and ammonium chloride (22.0 g., 0.4 mole) were dissolved in water (300 ml.) and alcohol (250 ml.) and kept at room temperature for 6 days. The dark solution was diluted with water (300 ml.) and saturated with hydrogen chloride. After a further 2 days 1-amino-cis-4-methylcyclo-hexanenitrile hydrochloride (62-2 g., 88%) had crystallized. This hydrochloride (60 g.) was refluxed with 20% hydrochloric acid for 12 hr. The solution was evaporated to dryness, and the residue extracted (Soxhlet) with ethanol-ether (9:1) for 8 hr. After removal of the solvent, the residue was basified with aqueous ammonia, to yield 1-amino-cis-4-methylcyclohexanecarboxylic acid (45.5 g.), needles [from acetic acid-water (1:1)], m. p. 356-360' (sublimes), $R_f$ 0.69 (Found: C, 61.6; H, 9.7; N, 8.4%. Calc. for $C_8H_{15}NO_2$: C, 61.1; H, 9.6; N, 8.9%).

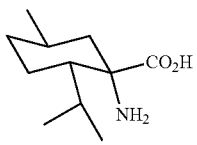

trans-2-Isopropyl-5-methylcyclohexane-1-spiro-5'-hydantoin

Prepared in 37% yield from natural (−)-menthone, this spiran formed needles (from ethanol), m. p. 228-231.5° (Found: C, 63.0%; H, 8.8%; N, 11.6%.)

1-Amino-trans-2-isopropyl-5-methylcyclohexanecarboxylc Acid

The previous hydantoin was hydrolysed by 60% sulphuric acid to the amino-acid, needles [from water-acetic acid (1:1)], m. p. 330° C. (Found: C, 66.0; H, 10.5; N, 6.8 for $C_{11}H_{21}NO_2$: requires C, 66.3; H, 10.6; N, 7.0%).

Dipeptide Fmoc-Asp(O$^t$Bu)-D-Phe-OH Synthesis

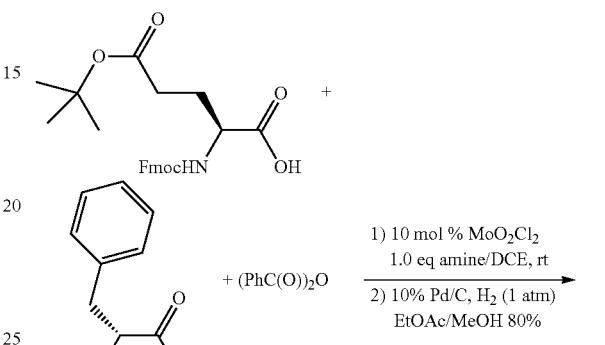

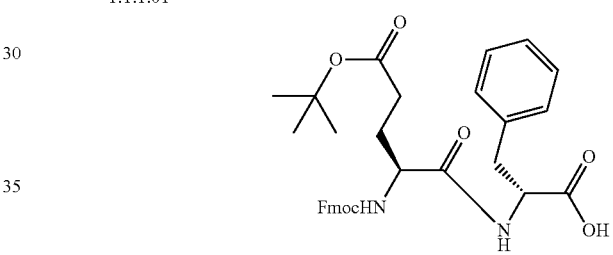

To a solution of Fmoc-Asp(O$^t$Bu)-OH (2.06 g, 5 mmol, 1.0 eq) in 1,2-dichloroethane (DCE, 10 mL) was added benzoic anhydride (1.14 g, 5.05 mmol, 1.01 eq) and MoO$_2$Cl$_2$ (100 mg, 0.5 mmol, 10 mol %) at room temperature under N$_2$ atmosphere and the reaction was monitored by TLC analysis. The reaction was stirred at room temperature for 2 h till the starting amino acid was totally consumed and cooled to 0° C. A solution of D-phenylalanine benzyl ester (1.275 g, 5.0 mmol, 1.0 eq) in 5 mL of DCE was added to the above solution via syringe follow by the addition of amine base (5.0 mmol, 1.0 eq) at 0° C. The reaction mixture was allowed stir at room temperature for 30 min. Solvent was evaporated, and the remaining residue was dissolved in EtOAc (100 mL), washed with saturated aqueous NaHCO$_3$ (30 mL), H$_2$O (30 mL), brine (30 mL), and dried over Na$_2$SO$_4$. After evaporation of solvent, the remaining residue was purified by flash chromatography on silica gel to provide Fmoc-Asp(O$^t$Bu)-D-Phe-OBn (2.68 g, 81% yield) as a white solid: TLC $R_f$=0.5 (EtOAc/Hexane=1/5); $^1$H NMR (400 MHz, CDCl$_3$): δ 7.77 (d, J=7.6, 2H), 7.57 (q, J=3.6, 2H), 7.41 (t, J=7.6, 2H), 7.35-7.32 (m, 4H), 7.30-7.27 (m, 4H), 7.17 (t, J=6.0, 3H), 7.02 (t, J=6.4, 3H), 5.83 (br, 1H), 5.13 (q, J=12.0, 2H), 4.87 (q, J=7.2, 1H), 4.58-4.49 (m, 1H), 4.36 (d, J=7.2, 2H), 4.20 (t, J=7.2, 1H), 3.10 (dd, J=16.4, 5.6, 2H), 1.43 (s, 9H); $^{13}$C NMR (100 MHz, CDCl$_3$) δ 170.8, 170.0, 156.0, 143.8, 143.6, 141.3, 135.5, 135.0, 129.2, 128.6, 128.5, 127.7, 127.1, 125.1, 120.0, 81.9, 67.3, 67.2, 53.4, 51.1, 47.0, 37.8, 37.3, 28.0; HRMS (ESI), Calcd. for $C_{40}H_{42}N_2NaO_7$ ([M+Na]$^+$): 685.2889, found: 685.2887.

To a solution of Fmoc-Asp(O$^t$Bu)-D-Phe-OBn (2.0 g, 3.0 mmol, 1 equiv) in 150 mL of 1/1 (v/v) ratio of EtOAc/MeOH was added 10% Pd/C (383 mg, 10 mol %) at RT. The reaction was allowed to stir in an atmosphere of hydrogen (balloon) over 1.5 h, following which it was filtered over Celite. The Celite was washed multiple times with MeOH (30 mL), EtOAc (30 mL) and the combined filtrate was concentrated in vacuo to give 1.699 g (99%) of dipeptide Fmoc-Asp(O$^t$Bu)-D-Phe-OH as a white solid. TLC $R_f$=0.23 (EtOAc/Hex=2/1)

$^1$H NMR (300 MHz, CDCl$_3$): δ 7.75 (d, J=7.5, 2H), 7.54 (d, J=7.2, 2H), 7.39 (t, J=7.5, 2H), 7.29 (d, J=7.2, 2H), 7.23-7.16 (m, 5H), 7.06 (d, J=7.5, 1H), 6.12 (d, J=8.7, 1H), 3.21 (dd, J=9.6, 6.3, 1H), 3.06 (dd, J=9.6, 6.6, 1H), 2.72 (dd, J=16.8, 6.3, 1H), 2.57 (dd, J=16.2, 5.7, 1H), 1.43 (s, 9H); $^{13}$C NMR (100 MHz, CDCl$_3$) δ 171.4, 170.8, 170.0, 156.0, 143.7, 143.6, 141.2, 135.7, 129.2, 128.5, 127.7, 127.1, 125.1, 120.0, 81.9, 67.3, 53.4, 52.3, 51.0, 47.0, 37.9, 37.4, 29.7, 28.0; HRMS (ESI), Calcd. for $C_{33}H_{36}N_2NaO_7$ ([M+Na]$^+$): 595.2420, found: 595.2423.

Dipeptide Fmoc-Arg(Mtr)-Gly-OCH$_3$ Synthesis by EDC-HOBt Coupling

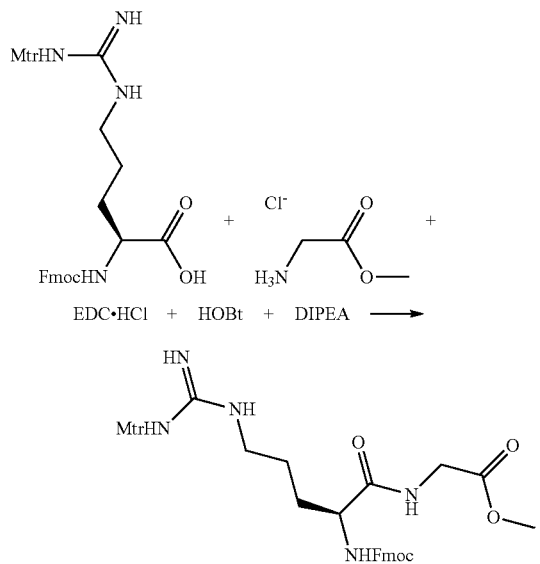

$^1$H NMR (400 MHz, CDCl$_3$): δ 7.72 (d, J=7.6, 2H), 7.63-7.54 (m, 3H), 7.25 (t, J=7.6, 2H), 7.24-7.22 (m, 1H), 6.49 (br, 1H), 6.40 (br, 1H), 6.07 (d, J=8.0 1H), 4.32 (q, J=6.8, 3H), 4.14 (t, J=7.2, 1H), 4.02 (dd, J=17.6, 5.2, 1H), 3.89 (dd, J=17.6, 5.2, 1H), 3.78 (s, 3H), 3.66 (s, 3H), 3.34-3.23 (m, 2H), 2.66 (s, 3H), 2.60 (s, 3H), 2.16 (s, 3H), 2.05 (s, 3H), 1.93 (t, J=6.0, 1H), 1.72-1.60 (m, 3H), 1.27 (t, J=6.8, 1H); $^{13}$C NMR (100 MHz, CDCl$_3$) 172.8, 170.6, 158.6, 156.5, 143.8, 143.7, 141.2, 138.5, 136.6, 134.7, 134.1, 133.0, 129.1, 127.7, 125.1, 124.9, 124.3, 120.3, 120.0, 111.7, 67.1, 60.4, 55.4, 52.3, 47.0, 41.0, 40.2, 31.9, 30.0, 29.7, 25.1, 24.0, 21.0, 18.3; HRMS (ESI), Calcd. for $C_{34}H_{41}N_5NaO_8S$ ([M+Na]$^+$): 702.2573, found: 702.2575.

Example 1

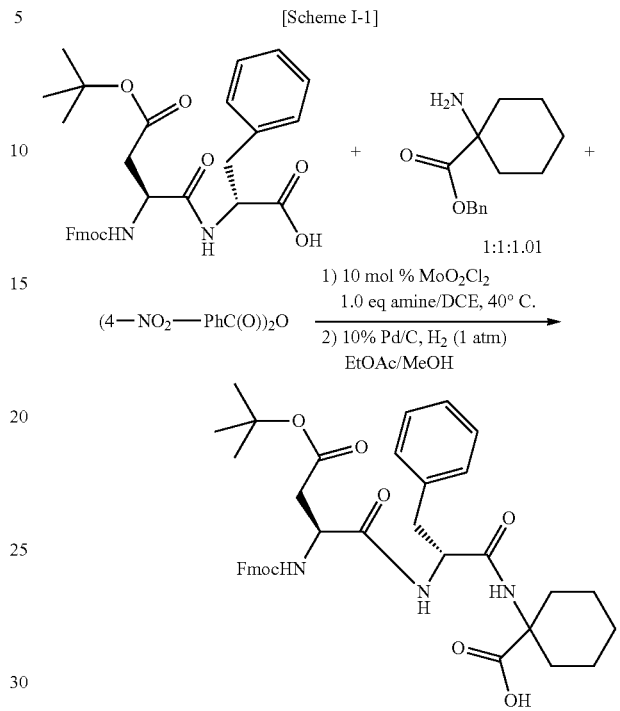

[Scheme I-1]

To a solution of Fmoc-Asp(O$^t$Bu)-D-Phe-OH (1.6 g, 2.8 mmol, 1.0 eq) in 1,2-dichloroethane (DCE, 5 mL) was added 2,6-dinitrobenzoic anhydride (974 mg, 2.82 mmol, 1.01 eq) and MoO$_2$Cl$_2$ (56 mg, 0.28 mmol, 10 mol %) at room temperature and gradually heated 40° C. under N$_2$ atmosphere and the reaction was monitored by TLC analysis. The reaction was stirred at 40° C. for 2 h till the starting amino acid was totally consumed and cooled to 0° C. A solution of 1-aminocyclohexanecarboxylic acid benzyl ester (653 mg, 2.8 mmol) in 3 mL DCE was added to the above solution via syringe follow by the addition of amine (2.8 mmol, 1.0 eq) at 0° C. The reaction mixture was allowed stir at room temperature for 12 h. Solvent was evaporated, and the remaining residue was dissolved in EtOAc, washed with saturated aqueous NaHCO$_3$ (1 mL), H$_2$O (1 mL), brine (1 mL), and dried over Na$_2$SO$_4$. After evaporation of solvent, the remaining residue was purified by silica gel flash chromatography to provide Fmoc-Asp(O$^t$Bu)-D-Phe-ACHA-OBn (1.69 g, 77% yield) as a white solid: TLC $R_f$=0.26 (EtOAc/Hexane=1/5); $^1$H NMR (400 MHz, CDCl$_3$): δ 7.77 (d, J=7.6, 2H), 7.57 (d, J=7.2, 2H), 7.41 (t, J=7.6, 2H), 7.35-7.27 (m, 7H), 7.24-7.16 (m, 5H), 6.95-7.89 (br, 1H), 6.21 (br, 1H), 5.72 (br, 1H), 5.11 (q, J=8.0, 2H), 4.63 (q, J=7.6, 1H), 4.43-4.21 (m, 3H), 4.23 (t, J=7.2, 1H), 3.07 (dd, J=16.4, 6.4, 1H), 2.98-2.92 (m, 1H), 2.81 (dd, J=162, 4.8, 1H), 2.64-2.53 (m, 1H), 1.85-1.79 (m, 4H), 1.64-1.49 (m, 3H), 1.47 (s, 9H), 1.26-1.20 (m, 4H); $^{13}$C NMR (100 MHz, CDCl$_3$) δ 173.5, 170.8, 170.5, 169.6, 143.6, 141.3, 136.0, 129.4, 128.7, 128.5, 128.2, 127.8, 127.1, 127.0, 125.0, 120.0, 82.0, 67.3, 66.8, 59.0, 54.1, 51.4, 47.1, 37.3, 32.3, 32.1, 28.0, 24.9, 21.2, 18.3; HRMS (ESI), Calcd. for $C_{47}H_{53}N_3NaO_8$ ([M+Na]$^+$): 810.3730, found: 810.3730.

To a solution of Fmoc-Asp(O$^t$Bu)-D-Phe-ACHA-OBn (1.5 g, 1.9 mmol, 1 equiv) in 100 mL of 1/1 (v/v) ratio of EtOAc/MeOH was added 10% Pd/C (242 mg, 10 mol %) at RT. The reaction was allowed to stir in an atmosphere of hydrogen (balloon) over 2 h, following which it was filtered over Celite. The Celite was washed multiple times with MeOH (20 mL), EtOAc (20 mL) and the combined filtrate was concentrated in vacuo to give 1.31 g (98%) of dipeptide Fmoc-Asp(O$^t$Bu)-D-Phe-ACHA-OH as a white solid: TLC R$_f$=0.24 (EtOAc/Hex=2/1); $^1$H NMR (400 MHz, CDCl$_3$): δ 7.75 (d, J=7.2, 2H), 7.73-7.72 (m, 6H), 7.40-7.32 (m, 5H), 7.31-7.21 (m, 6H), 6.83 (d, J=16.0, 1H), 6.46 (d, J=5.4, 1H), 6.03 (br, 1H), 4.73 (q, J=7.6, 1H), 4.48-4.42 (m, 1H), 4.41-4.12 (m, 4H), 3.19-3.02 (m, 2H), 2.84-2.68 (m, 2H), 2.18-1.65 (m, 6H), 1.49 (s, 9H), 1.63-1.24 (m, 10H); $^{13}$C NMR (100 MHz, CDCl$_3$) δ 176.6, 171.6, 171.3, 171.1, 170.7, 156.2, 143.7, 141.2, 136.6, 136.5, 129.3, 128.6, 127.7, 127.1, 126.9, 125.1, 120.0, 81.7, 67.5, 59.4, 54.7, 52.1, 51.6, 47.0, 38.0, 37.3, 36.9, 36.7, 32.9, 31.0, 29.7, 28.0, 25.0, 21.3, 21.1; HRMS (ESI), Calcd. for C$_{40}$H$_{47}$N$_3$NaO$_8$ ([M+Na]$^+$): 720.3260, found: 720.3257.

In a dry 50-mL, two-necked, round-bottomed flask was charged with MoO$_2$Cl$_2$ (5.0 mg, 0.025 mmol, 20 mol %) in anhydrous CH$_2$Cl$_2$ (1.0 mL). To the above solution, Fmoc-1-aminocyclohexane-1-carboxylic acid (2-1) (48.3 mg, 0.125 mmol) was added at ambient temperature followed by addition of benzoic anhydride (29 mg, 0.127 mmol), and heated at 40° C. for 6 h then cooled to 0° C.

A solution of D-Phe-Asp(OtBu)-OMe (48.3 mg, 0.125 mmol) in DCM (0.5 mL) was added to above solution at 0° C. and gradually raise temperature to rt and stir at rt for 2 h. Afterward 14 μL of 2,6-lutidine was added and continued stirred for additional 4 h at rt. The reaction was quenched with water (2 mL) and the organic phase was separated and the aqueous phase was extracted with dichloromethane (10 mL×2). The combined organic phase were dried over anhydrous Na$_2$SO$_4$ and concentrated. The crude product was purified by column chromatography on silica gel (EA/Hex=2/3) and gave Fmoc-protected tripeptide (3'-1) (58 mg, 67%).

The procedure for preparing the tripeptide (3') is not limited to the above procedure, and Fmoc-protected tripeptide (3'-1) can be prepared, for example, by the following Scheme I'-2-1.

[Scheme I'-1-1]

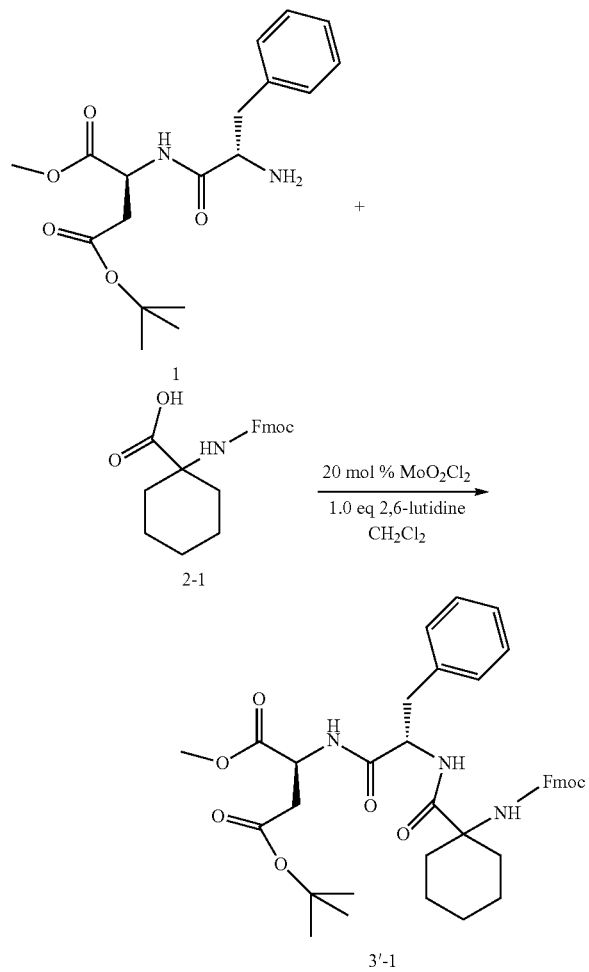

A solution of H-D-Phe-Asp(OtBu)-OMe.HCl (1-HCl) (48.7 mg, 0.126 mmol, 1.01 eq) in MeOH (1 mL) was cooled to 0° C., 1.5 eq NaHCO$_3$ was added and stirred for 0.5 h at rt. MeOH was evaporated and the resulting residual was dissolved in 2 mL THF and dried with Na$_2$SO$_4$, and filtered. The solvent was removed and dried under vacuum to obtain D-Phe-Asp(OtBu)-OMe (1).

[Scheme I'-2-1]

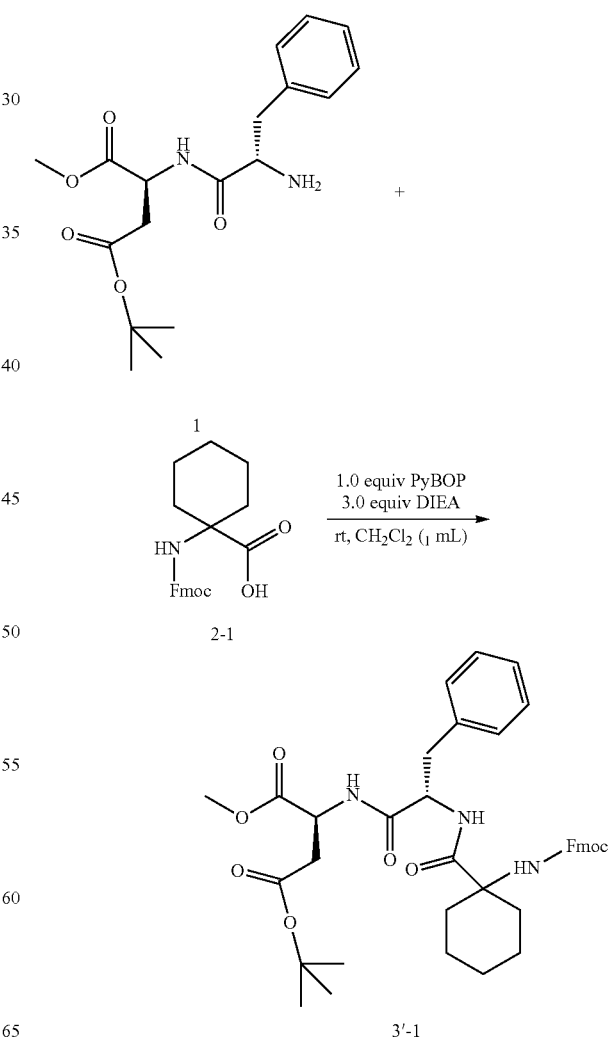

In a dry 25-mL, two-necked, round-bottomed flask was charged with coupling reagent (1.0 equiv) in DCM (1 mL/mmol) and treated under stirring with DIEA (3.0 equiv) at 0° C. for 5 min. Fmoc-1-aminocyclohexane-1-carboxylic acid (2-1) (182.7 mg, 0.5 mmol) was added at 0° C. for 10 min, and mixed with H-D-Phe-Asp(OtBu)-OMe.HCl (1) (192.7 mg, 0.55 mmol). The ice bath was removed after 10 min and the stirring continued at room temperature 96 h. The mixture was poured into AcOEt (50× the DCM volume) and the solution treated according to the usual workup. The crude product was purified by column chromatography on silica gel and gave Fmoc-protected tripeptide (3'-1). Yield: 68%

Purified by column chromatography (EtOAc/hexanes=3:7, $R_f$=0.2) $^1$H NMR (400 MHz, CDCl$_3$) δ 7.74 (d, J=7.2 Hz, 2H), 7.57 (d, J=7.2 Hz, 2H), 7.40-7.27 (m, 4H), 7.19-7.07 (m, 5H), 6.63 (d, J=8.0 Hz, 1H), 5.11 (s, 1H), 4.84 (d, J=6.6 Hz, 1H), 4.74 (d, J=5.4 Hz, 1H), 4.41-4.32 (m, 2H), 4.15 (t, J=6.4 Hz, 1H), 3.59 (s, 3H), 3.23 (dd, J=14.0, 6.9 Hz, 1H), 3.04 (dd, J=14.0, 8.2 Hz, 1H), 2.76-2.63 (m, 2H), 1.92-1.77 (m, 2H), 1.60-1.47 (m, 5H), 1.38 (s, 9H), 1.27-1.18 (m, 3H); $^{13}$C NMR (100 MHz, CDCl$_3$) δ 173.8, 171.2, 170.6, 169.2, 155.3, 143.6, 143.5, 141.1, 136.6, 128.9, 128.3, 127.6, 126.9, 126.9, 124.8, 124.8, 119.8, 119.8, 81.3, 66.7, 59.3, 53.5, 52.1, 48.7, 47.0, 37.2, 37.0, 32.4, 30.9, 27.7, 24.8, 21.1, 21.0; HRMS (ESI) calcd for C$_{40}$H$_{47}$N$_3$O$_8$ (M+$^+$Na): 720.3255; found: 720.3253.

A solution of 200 mg (0.28 mmol) of the Fmoc-protected tripeptide (3'-1) was treated with 20% piperidine in DCM (1 mL) for 1 hour at room temperature. After removal of piperidine by coevaporation with methanol, the crude product was dried in vacuo and purified by column chromatography on silica gel to obtain tripeptide (3-1).

Yield: 106.8/136.2=78%

Purified by column chromatography (EtOAc/hexanes=9:1, $R_f$=0.2) $^1$H NMR (400 MHz, CDCl$_3$) δ 8.21 (d, J=8.2 Hz, 1H, NH), 7.21 (t, J=6.8 Hz, 2H), 7.16-7.14 (m, 3H), 7.05 (d, J=8.4 Hz, 1H), 4.76-4.72 (m, 1H), 4.63-4.58 (m, 1H), 3.66 (s, 3H, OCH$_3$), 3.15 (dd, J=14.0, 6.2 Hz, 1H), 3.00 (dd, J=14.0, 8.0 Hz, 1H), 2.81 (dd, J=16.0, 4.0 Hz, 1H), 2.51 (dd, J=16.0, 4.0 Hz, 1H), 1.97-1.72 (m, 2H), 1.58-1.51 (m, 4H), 1.35 (s, 9H, C(CH$_3$)$_3$), 1.36-1.28 (m, 2H), 1.24-1.09 (m, 2H); $^{13}$C NMR (100 MHz, CDCl$_3$) δ 178.3, 170.9, 170.8, 169.9, 136.8, 129.1, 128.3, 126.6, 81.7, 57.1, 53.8, 52.4, 48.2, 37.5, 37.1, 34.4, 34.1, 27.0, 25.0, 21.0; HRMS (ESI) calcd for C$_{25}$H$_{38}$N$_3$O$_6$ (M$^+$+Na): 476.2755; found: 476.2753.

Example 2

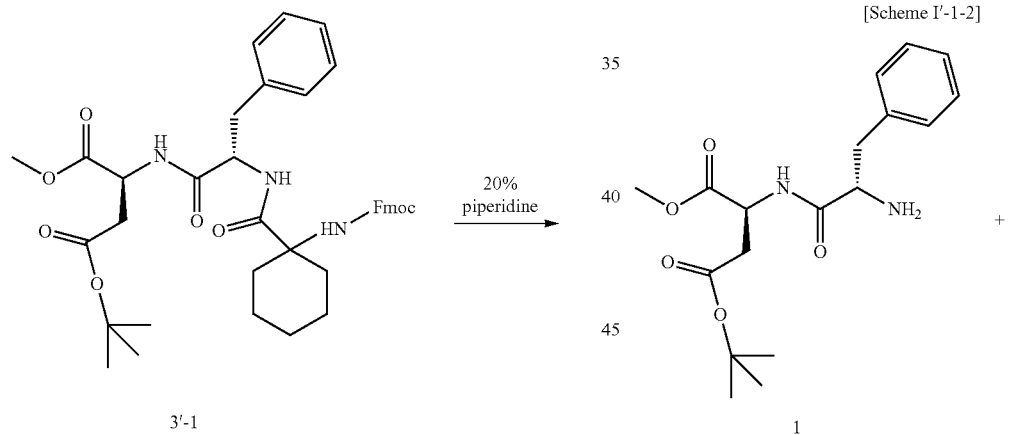

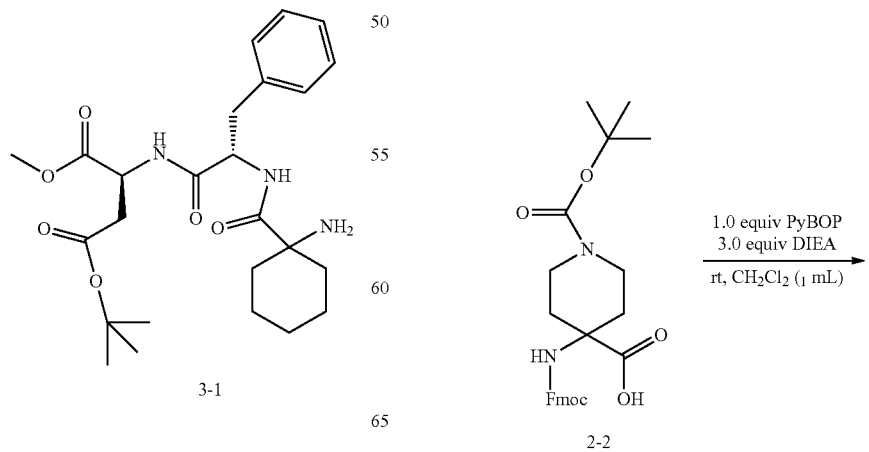

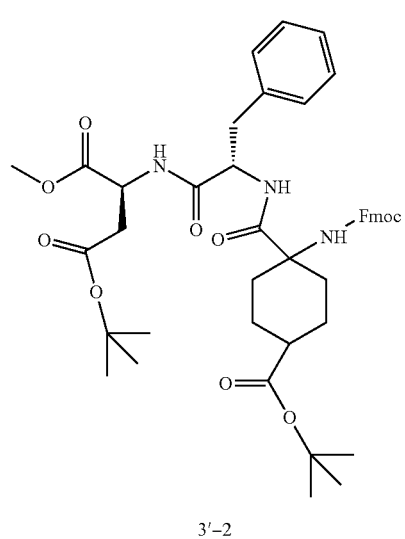

3'-2

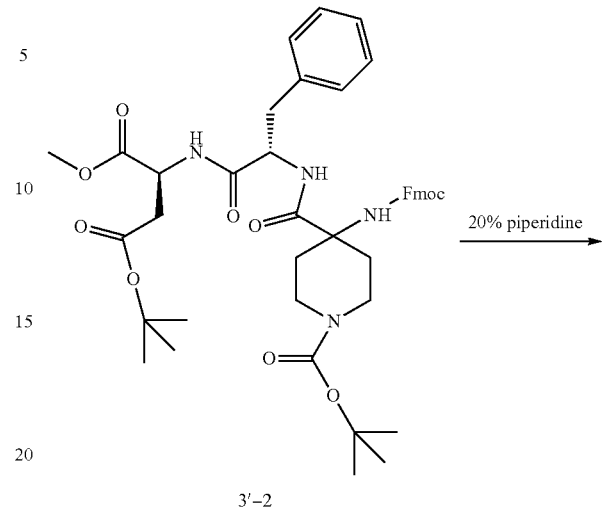

[Scheme I'-3-2]

20% piperidine →

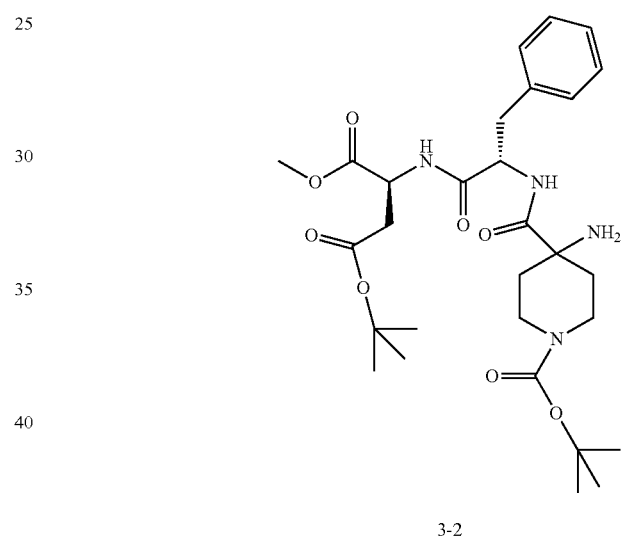

3-2

In a dry 25-mL, two-necked, round-bottomed flask was charged with coupling reagent (1.0 equiv) in DCM (1 mL/mmol) and treated under stirring with DIEA (3.0 equiv) at 0° C. for 5 min. 1-Boc-piperidine-4-Fmoc-amino-1-carboxylic acid (2-2) (233.27 mg, 0.5 mmol) was added at 0° C. for 10 min, and mixed with H-D-Phe-Asp(OtBu)-OMe.HCl (1) (202.91 mg, 0.525 mmol). The ice bath was removed after 10 min and the stirring continued at room temperature 96 h. The mixture was poured into AcOEt (50× the DCM volume) and the solution treated according to the usual workup. The crude product was purified by column chromatography on silica gel and gave Fmoc-protected tripeptide (3'-2).

Yield: 259/399.17=65%

Purified by column chromatography (EtOAc/hexanes=3:7, $R_f$=0.2) $^1$H NMR (400 MHz, CDCl$_3$) δ 7.75 (d, J=7.6 Hz, 2H), 7.56 (t, J=5.2 Hz, 2H), 7.39 (dt, J=6.4, 2.4 Hz, 2H), 7.32-7.27 (m, 2H), 7.19 (t, J=7.6 Hz, 2H), 7.12 (t, J=6.2 Hz, 3H), 6.68 (d, J=7.6 Hz, 1H), 4.79 (s, 1H), 4.44 (d, J=6.0 Hz, 1H), 4.15 (t, J=6.2 Hz, 1H), 3.74-3.67 (m, 1H), 3.63 (s, 3H), 3.56 (d, J=14.0 Hz, 1H), 3.19 (br, 1H), 2.99 (dd, J=14.0, 8.2 Hz, 1H), 2.89 (br, 1H), 2.76 (dd, J=16.0, 6.0 Hz, 1H), 2.60 (d, J=12.8 Hz, 1H), 2.05-1.96 (m, 1H), 1.77-1.53 (m, 6H), 1.42 (s, 9H), 1.38 (s, 9H); $^{13}$C NMR (100 MHz, CDCl$_3$) δ 172.7, 171.2, 170.5, 169.3, 155.3, 154.3, 143.5, 143.4, 141.1, 136.5, 128.9, 128.3, 127.6, 126.9, 126.9, 126.7, 124.8, 124.7, 119.8, 81.4, 79.6, 66.7, 57.6, 53.6, 52.3, 48.7, 46.9, 37.1, 28.2, 27.8.

A solution of 219 mg (0.27 mmol) of the Fmoc-protected tripeptide (3'-2) was treated with 20% piperidine in DCM (1 mL) for 3 hour at room temperature. After removal of piperidine by coevaporation with methanol, the crude product was dried in vacuo and purified by column chromatography on silica gel to obtain tripeptide (3-2).

Yield: 113/155.6=72%

Purified by column chromatography (EtOAc/hexanes=9:1, $R_f$=0.2) $^1$H NMR (400 MHz, CDCl$_3$) δ 8.05 (d, J=8.2 Hz, 1H, NH), 7.26-7.14 (m, 5H), 7.05 (d, J=8.4 Hz, 1H), 4.76-4.72 (m, 1H), 4.66-4.60 (m, 1H), 3.88-3.76 (m, 2H, NH$_2$), 3.67 (s, 3H, OCH$_3$), 3.16 (dd, J=14.0, 6.2 Hz, 1H), 3.02-2.92 (m, 3H), 2.82 (dd, J=17.0, 4.4 Hz, 1H), 2.52 (dd, J=17.0, 4.6 Hz, 1H), 2.07-2.00 (m, 1H), 1.91-1.84 (m, 1H), 1.58-1.38 (m, 1H), 1.40 (s, 9H, C(CH$_3$)$_3$), 1.36 (s, 9H, C(CH$_3$)$_3$), 1.32-1.20 (m, 2H), 1.11-1.06 (m, 1H); $^{13}$C NMR (100 MHz, CDCl$_3$) δ 176.7, 170.9, 170.6, 169.9, 154.4, 136.6, 129.1, 128.4, 126.7, 81.7, 79.4, 55.3, 53.7, 52.4, 48.2, 37.5, 37.0, 34.2, 28.2, 27.8; HRMS (ESI) calcd for C$_{29}$H$_{45}$N$_4$O$_8$ (M$^+$+1): 577.3232; found: 577.3248.

Example 3

[Scheme II]

Fmoc-Asp(O'Bu)-D-Phe-ACHA-Arg(Mtr)-Gly-OCH₃ synthesis

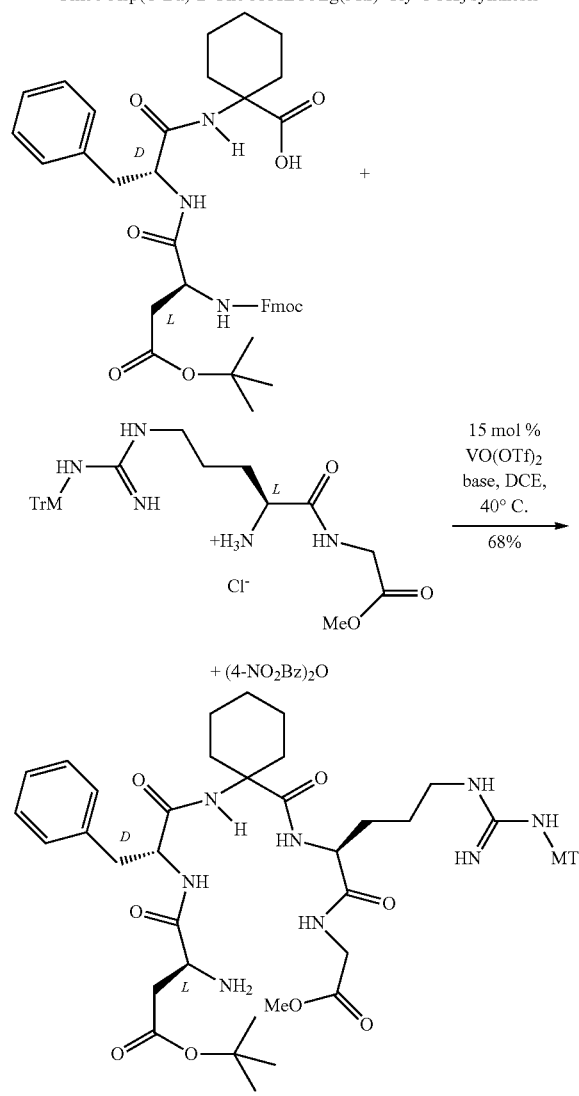

To a solution of Fmoc-Asp(O'Bu)-D-Phe-ACHA-OH (698 g, 1 mmol, 1.0 eq) in 1,2-dichloroethane (DCE, 5 mL) was added 2,6-dinitrobenzoic anhydride (348 mg, 1.01 mmol, 1.01 eq) and VO(OTf)₂ (55 mg, 0.15 mmol, 15 mol %) at room temperature and gradually heated 40° C. under N₂ atmosphere and the reaction was monitored by TLC analysis. The reaction was stirred at 40° C. for 4 h till the starting amino acid was totally consumed and cooled to 0° C. A solution of NH₂-Arg(Mtr)-Gly-OCH₃ (457 mg, 1 mmol) in 3 mL DCE was added to the above solution via syringe follow by the addition of base (1.0 mmol, 1.0 eq) at 0° C. The reaction mixture was allowed stir at room temperature for 12 h. Solvent was evaporated, and the remaining residue was dissolved in EtOAc (100 mL), washed with saturated aqueous NaHCO₃ (20 mL), H₂O (20 mL), brine (20 mL), and dried over Na₂SO₄. After evaporation of solvent, the remaining residue was purified by flash chromatography on silica gel to provide Fmoc-Asp(OBu)-D-Phe-ACHA-Arg(Mtr)-Gly-OCH₃ (612 mg, 68% yield) as a white solid: TLC $R_f$=0.50 (EtOAc/Hexane=3/1); $^1$H NMR (400 MHz, CDCl₃): δ 7.75 (d, 2H, J=−7.20 Hz), 7.57 (m, 2H), 7.39 (t, 2H, J=7.6 Hz), 7.30-7.18 (m, 7H), 6.60 (br, 1H), 6.55 (br, 1H), 4.67 (br, 1H), 4.52-4.42 (m, 1H), 4.37 (q, 1H, 0.1-6.40 Hz), 4.35-4.23 (m, 1H), 4.19 (t, 1H, J=7.2 Hz), 4.14-4.04 (m, 1H), 3.81 (s, 3H), 3.69-3.61 (m, 1H), 3.58 (s, 3H), 3.46-3.42 (m, 1H), 3.21-3.09 (m, 1H), 3.03-2.92 (m, 1H), 2.68 (s, 3H), 2.59 (s, 3H), 2.25-2.11 (m, 1H), 2.10 (s, 3H), 2.04-1.83 (m, 4H), 1.79-1.58 (m, 3H), 1.59-1.41 (m, 2H), 1.39 (s, 9H), 1.35-1.05 (2H); $^{13}$C NMR (100 MHz, CDCl₃) δ175.4, 172.9, 172.6, 172.0, 171.2, 170.5, 156.7, 143.6, 141.2, 136.3, 129.2, 129.0, 128.7, 127.8, 127.1, 127.0, 125.0, 120.0, 112.3, 81.7, 77.3, 67.2, 60.4, 55.5, 53.0. 52.3, 51.2, 47.0, 41.2, 37.0, 36.7, 34.1, 30.0, 29.0, 28.0, 24.9, 24.3, 21.3, 20.9, 18.3, 12.0; HRMS (ESI), calculated for $C_{58}H_{74}N_8O_{13}S$ ([M+Na]$^+$): 1145.4994, found: 1145.4981.

[Scheme II'-1]

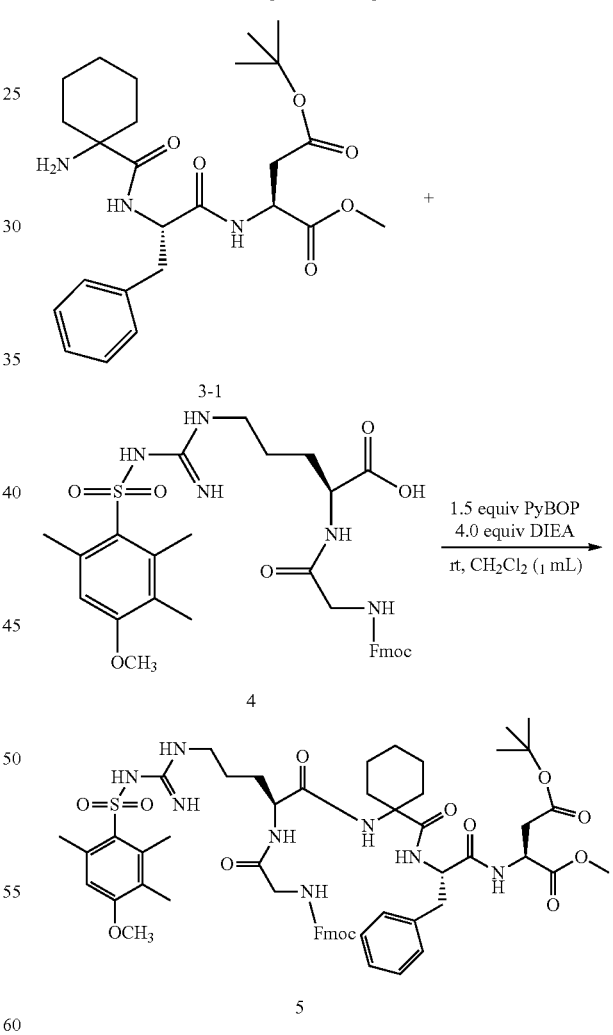

In a dry 25-mL, two-necked, round-bottomed flask was charged with coupling reagent (1.5 equiv) in DCM (1 mL/mmol) and treated under stirring with DIEA (4.0 equiv) at 0° C. for 5 min. Fmoc-Gly-Arg(Mtr)-OH (4) (149.6 mg, 0.22 mmol) was added at 0° C. for 20 min, and mixed with tripeptide (3-1) (106.8 mg, 0.22 mmol). The ice bath was removed after 20 min and the stirring continued at room temperature 10 days. The crude product was dried in vacuo and purified by column chromatography on silica gel to obtain Fmoc-protected peptide (5).

Yield: 30% (PyBOP); 65% (by MoO$_2$Cl$_2$/4-nitrobenzoic anhydride).

Purified by column chromatography (EtOAc/MeOH=9.5:0.5, R$_f$=0.6); $^1$H NMR (400 MHz, CDCl$_3$) δ 7.76 (d, J=8.0, 1H, NH), 7.70 (d, J=8.2, 2H), 7.56 (d, J=6.4, 1H), 7.51 (d, J=7.2, 2H), 7.42 (bd, 1H, NH), 7.38 (d, J=8.0, 2H), 7.36-7.16 (m, 6H), 7.11-7.06 (m, 5H), 6.86 (d, J=7.6 Hz, 1H, NH), 6.50 (s, 1H), 6.38 (bs, 2H), 4.84 (dd, J=14.0, 6.6 Hz, 1H), 4.67 (dd, J=13.8, 8.0 Hz, 1H), 4.45-4.27 (m, 3H), 4.20-4.11 (m, 1H), 3.90-3.89 (m, 2H), 3.79 (s, 3H, OCH$_3$), 3.73-3.71 (m, 1H), 3.65 (s, 3H, OCH$_3$), 3.54-3.46 (m, 1H), 3.43-3.36 (m, 2H), 3.20-3.16 (m, 1H), 3.05 (dd, J=14.0, 9.3 Hz, 1H), 2.71 (t, J=8.0 Hz, 1H), 2.71 (m, 1H), 2.67 (s, 3H, CH$_3$), 2.61 (s, 3H, CH$_3$), 2.10 (s, 3H, CH$_3$), 2.01-1.79 (m, 6H), 1.76-1.51 (m, 8H), 1.50-1.41 (m, 6H), 1.39 (s, 9H, C(CH$_3$)$_3$), 1.32-1.02 (m, 8H), 0.94-0.82 (m, 2H); HRMS (ESI) calcd for C$_{58}$H$_{74}$N$_8$O$_{13}$S (M+$^+$H): 1122.5098; found: 1122.5096.

[Scheme II'-2]

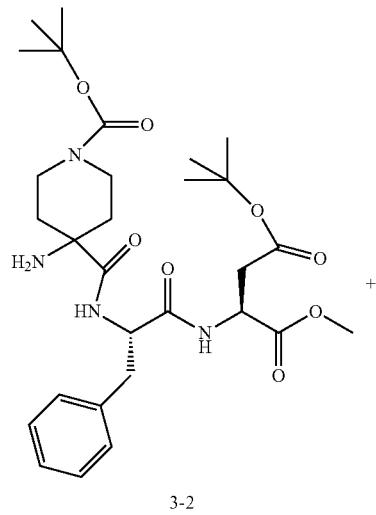

3-2

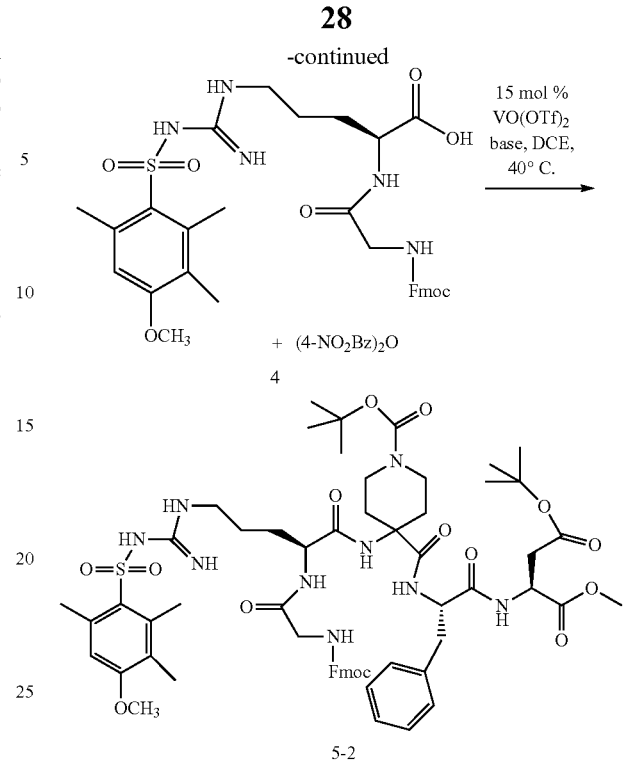

5-2

Similar procedure like the one for [Scheme II] provide the product in 72% yield: Purified by column chromatography (EtOAc/MeOH=9.5:0.5, R$_f$=0.4); $^1$H NMR (400 MHz, CDCl$_3$) δ 7.62 (d, J=8.2, 1H, NH), 7.60 (d, J=8.0, 2H), 7.53 (d, J=6.4, 1H), 7.45 (d, J=7.2, 2H), 7.30 (bd, 1H, NH), 7.36 (d, J=8.0, 2H), 7.34-7.18 (m, 6H), 7.18-7.10 (m, 5H), 6.74 (d, J=7.6 Hz, 1H, NH), 6.40 (s, 1H), 6.25 (bs, 2H), 4.81 (dd, J=13.8, 6.8 Hz, 1H), 4.70 (dd, J=13.8, 8.0 Hz, 1H), 4.52-4.31 (m, 3H), 4.18-4.08 (m, 1H), 3.95-3.86 (m, 2H), 3.77 (s, 3H, OCH$_3$), 3.73-3.71 (m, 1H), 3.62 (s, 3H, OCH$_3$), 3.68-3.60 (m, 2H), 3.57-3.46 (m, 1H), 3.48-3.36 (m, 2H), 3.18-3.12 (m, 1H), 3.08 (t, J=8.0 Hz, 1H), 2.71 (dd, J=14.0, 9.3 Hz, 1H), 2.73-2.67 (m, 1H), 2.63 (s, 3H, CH$_3$), 2.55 (s, 3H, CH$_3$), 2.11 (s, 3H, CH$_3$), 2.11-1.83 (m, 6H), 1.76-1.61 (m, 8H), 1.55-1.45 (m, 6H), 1.36 (s, 9H, C(CH$_3$)$_3$), 1.36-1.06 (m, 81H), 0.92-0.84 (m, 2H); HRMS (ESI) calcd for C$_{62}$H$_{82}$N$_9$O$_{15}$S (M+$^+$H): 1224.5646; found: 1224.5662.

Example 4

[Scheme III]

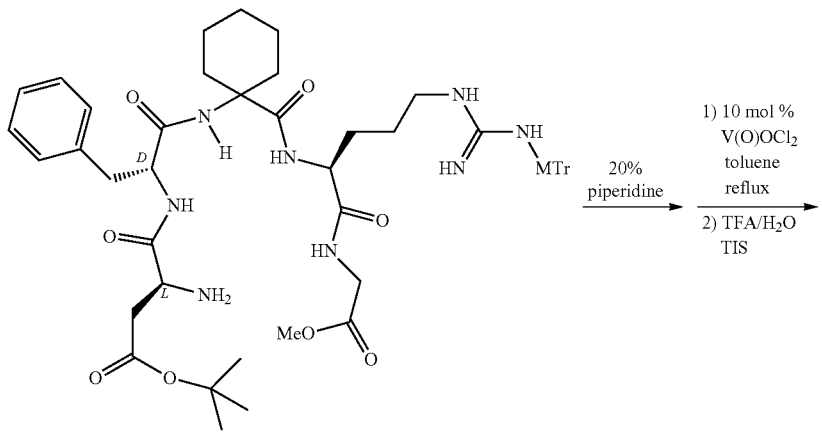

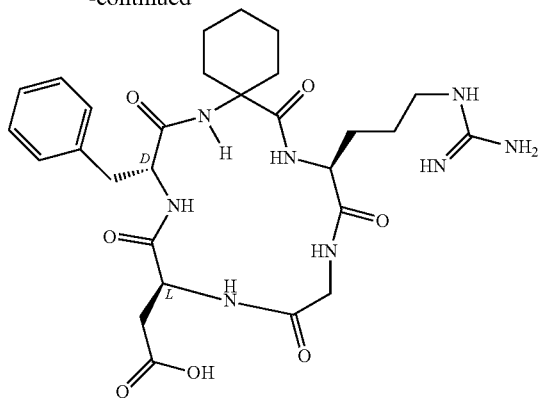
After Fmoc, MTR, and t-Boc Deprotection:
$^1$H NMR (400 MHz, CDCl$_3$) δ 10.02 (bs, 2H, G-NH$_2$), 8.25 (bs, 1H, G-NH), 7.83 (bd, J=8.2, 1H, amide NH), 7.75 (d, J=8.0, 1H, amide NH), 7.71 (d, J=8.4, 11H, amide NH), 7.62 (t, J=8.0, 1H, amide NH), 7.36 (d, J=8.2, 1H, amide NH), 7.22-7.11 (m, 5H, Ph), 4.72 (dd, J=15.8, 7.8, 1H), 4.55 (bt, 1H), 4.36 (bs, 2H), 4.20 (dd, J=16.0, 7.2, 1H), 3.36 (t, J=14.8 Hz, 2H), 3.25-3.12 (m, 4H), 2.64 (dd, J=7.6, 16.0 Hz, 1H), 2.57 (dd, J=16.0, 10.4, 1H), 1.84-1.72 (m, 4H), 1.58-1.50 (m, 4H), 1.48-1.38 (m, 4H); HRMS (ESI) calcd for C$_{28}$H$_{41}$N$_8$O$_7$ (M$^+$+H): 601.3098; found: 601.3094; HPLC analysis: (C18, 250×4.6 mm, 0.5 (mL/min), λ=254 nm). a.1% TFA in H$_2$O/ACN (95:5) 30 min; b.1% TFA in H$_2$O/ACN (5:95) 31-60 min; t$_R$ 36.71, 46.17 min.
[Scheme III'-1]
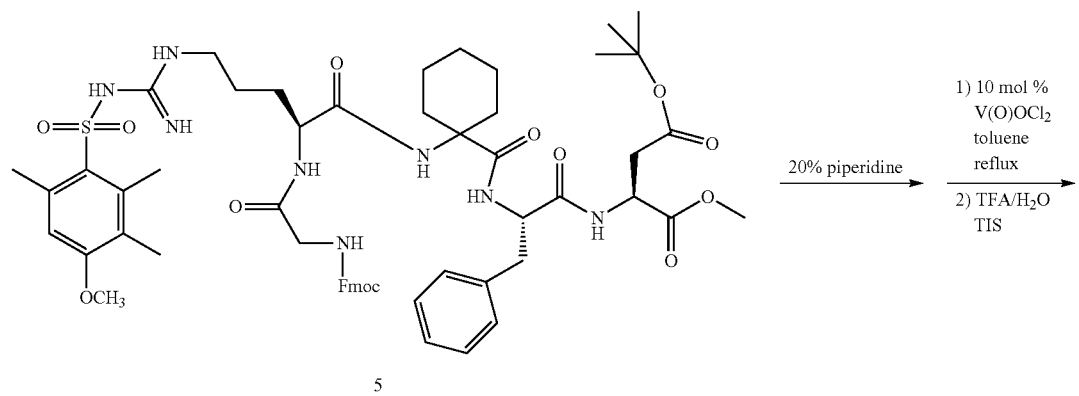
5
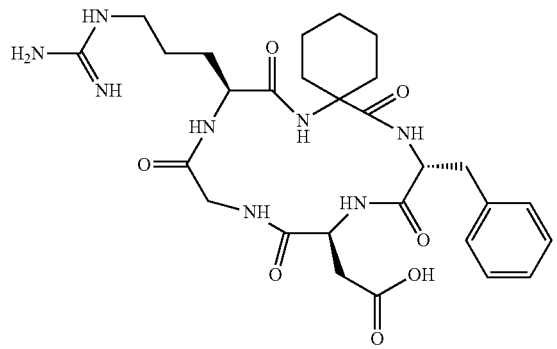
6

A solution of 40.5 mg (0.036 mmol) of the Fmoc-protected peptide (5) was treated with 20% piperidine in DCM (1 mL) for 1 hour at room temperature. After removal of piperidine by coevaporation with methanol, the crude product was dried in vacuo and purified by column chromatography on silica gel. The resulting product was subjected to intramolecular amide bond formation by treatment with 10 mol % VOOCl$_2$ V(O)(acac)$_2$, or Ti(O)(acac)$_2$ in refluxed toluene for 18 h. The resulting crude mixture was cooled to ambient temperature and concentrated. The crude residue was dissolved in trifluoroacetic acid (5 mL) and H$_2$O (1 mL) and then treated with thioanisole (1 mL). The mixture was induced precipitation with di-isopropyl ether (5 mL) and the solid washed with di-isopropyl ether and dried in vacuo to obtain the cyclopeptide (6). The cyclic pentapeptide can be further purified by HPLC on a reverse phase C-18 column (gradient: 95/5 to 80/20, H$_2$O/CH$_3$CN) to give 18 mg (69% yield) of pure 6.

Before MTr and t-Boc Deprotection:

$^1$H NMR (400 MHz, CDCl$_3$) δ 7.68-7.287 (m, 1H, imine), 7.22-7.12 (m, 5H, Ph group), 6.50 (s, 1H, amide), 6.33 (br, 2H, amide), 4.80 (dd, J=6.0, 6.9 Hz, 1H), 4.59-4.55 (m, 1H), 4.45-4.36 (m, 1H), 3.80 (s, 3H, OCH$_3$-Ph), 3.33-3.15 (m, 3H), 2.79 (t, J=8.4 Hz, 1H), 2.65 (s, 3H, CH$_3$-Ph), 2.59 (s, 3H, CH$_3$-Ph), 2.31 (t, J=10.4 Hz, 1H), 2.08 (s, 3H, CH$_3$-Ph), 2.03-1.95 (m, 4H), 1.64-1.41 (m, 5H), 1.36 (s, 9H, tBu), 1.30-1.27 (m, 2H), 1.25-1.22 (m, 4H); R$_f$ 0.5 (EtOAc/MeOH, 9/1); HRMS (ESI) calcd for C$_{42}$H$_{60}$N$_8$O$_{10}$S (M$^+$+H): 868.4153; found: 869.4233.

After Deprotection:

$^1$H NMR (400 MHz, CDCl$_3$) δ 10.12 (bs, 2H, G-NH$_2^+$), 8.22 (bs, 1H, G-NH), 7.79 (bd, J=8.4, 1H, amide NH), 7.72 (d, J=8.2, 1H, amide NH), 7.68 (d, J=8.2, 1H, amide NH), 7.58 (t, J=8.0, 1H, amide NH), 7.41 (d, J=8.2, 1H, amide NH), 7.24-7.13 (m, 5H, Ph), 4.68 (dd, J=13.2, 6.8, 1H), 4.45 (bt, 1H), 4.30 (bs, 2H), 4.22 (dd, J=16.0, 7.2, 1H), 3.30 (t, J=14.0 Hz, 2H), 3.18-3.00 (m, 4H), 2.68 (dd, J=7.6, 16.0 Hz, 1H), 2.55 (dd, J=16.0, 10.4, 1H), 1.78-1.01 (m, 10H); HRMS (ESI) calcd for C$_{28}$H$_{41}$N$_8$O$_7$ (M$^+$+H): 601.3098; found: 601.3090; HPLC analysis: (C18, 250×4.6 mm, 0.5 (mL/min), λ=254 nm). a.1% TFA in H$_2$O/ACN (90:10) 30 min; b.1% TFA in H$_2$O/ACN (10:90) 31-60 min; t$_R$ 34.6, 42.6 min.

[Scheme III'-2]

After Fmoc, MTR, and t-Boc Deprotection:

$^1$H NMR (400 MHz, CDCl$_3$) δ 9.68 (bs, 2H, G-NH$_2^+$), 8.09 (bs, 1H, G-NH), 7.68 (bd, J=8.4, 1H, amide NH), 7.64 (d, J=8.2, 1H, amide NH), 7.60 (d, J=8.2, 1H, amide NH), 7.50 (t, J=8.0, 1H, amide NH), 7.45 (d, J=8.2, 1H, amide NH), 7.27-7.16 (m, 5H, Ph), 4.65 (dd, J=15.8, 7.6, 1H), 4.72 (bt, 1H), 4.27 (bs, 2H), 4.15 (dd, J=15.8, 7.4, 1H), 3.32 (t, J=15.2 Hz, 2H), 3.24-3.15 (m, 4H), 2.80-2.65 (m, 4H), 2.64 (dd, J=7.6, 16.0 Hz, 1H), 2.58 (dd, J=16.0, 10.4, 1H), 2.14-2.06 (m, 2H), 2.05 (bs, 1H, NH), 1.89-1.82 (m, 2H), 1.78-1.72 (m, 4H), 1.67-1.48 (m, 2H); HRMS (ESI) calcd for C$_{27}$H$_{40}$N$_9$O$_7$ (M$^+$+H): 601.2972; found: 601.2970; HPLC analysis: (C18, 250×4.6 mm, 0.5 (mL/min), λ=254 nm). a.1% TFA in H$_2$O/ACN (90:10) 20 min; b.1% TFA in H$_2$O/ACN (5:95) 31-60 min; t$_R$ 41.8, 50.4 min.

Although the present invention has been explained in relation to its preferred embodiment, it is to be understood that many other possible modifications and variations can be made without departing from the spirit and scope of the invention as hereinafter claimed.

What is claimed is:

1. A cyclopeptide represented by any one of the following formulas (I-1) to (I-4):

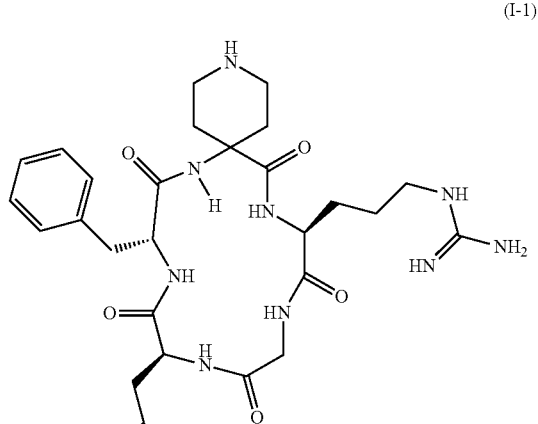

(I-1)

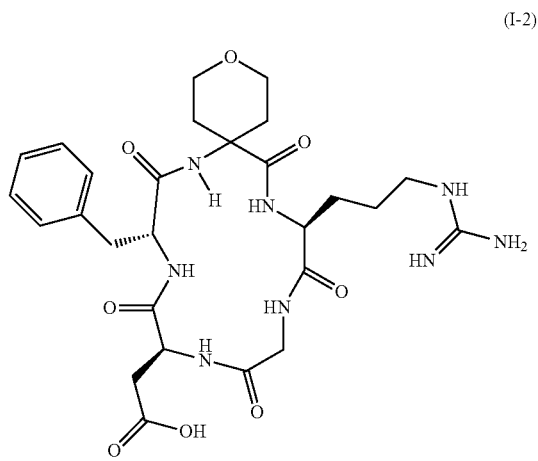

(I-2)

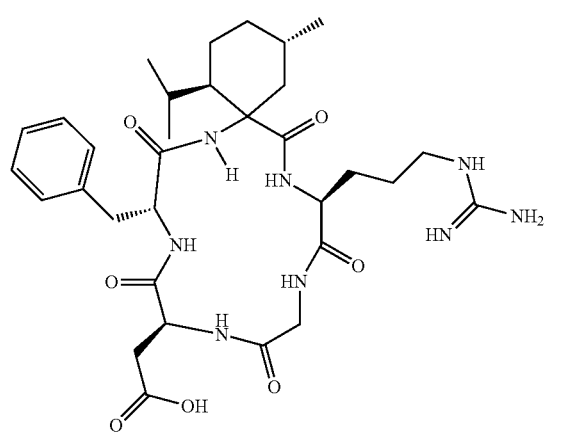

(I-3)

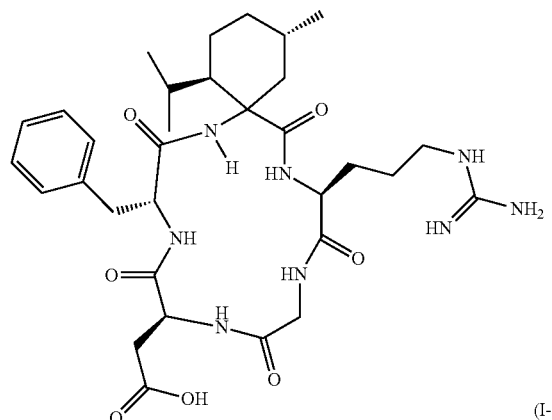

(I-3)

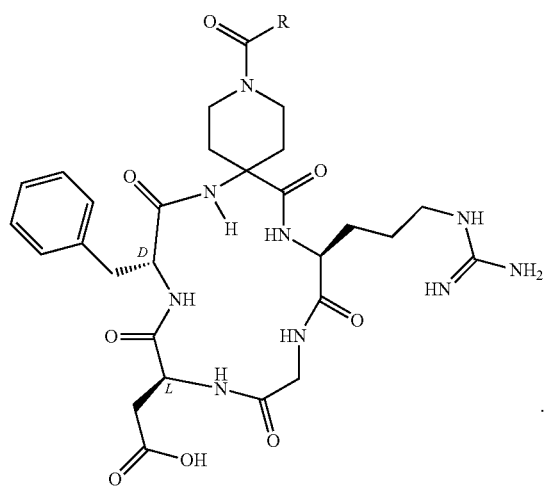

(I-4)

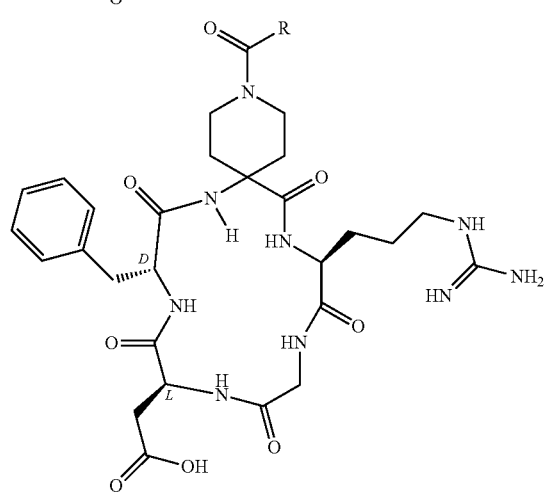

(I-4)

2. A pharmaceutical or cosmetic composition, comprising:
   a cyclopeptide represented by any one of the following formulas (I-1) to (I-4); and
   an excipient.

3. A method for preparing a cyclopeptide, comprising the following steps:
   (A) providing a compound represented by formulas (I-1) and (II-2):

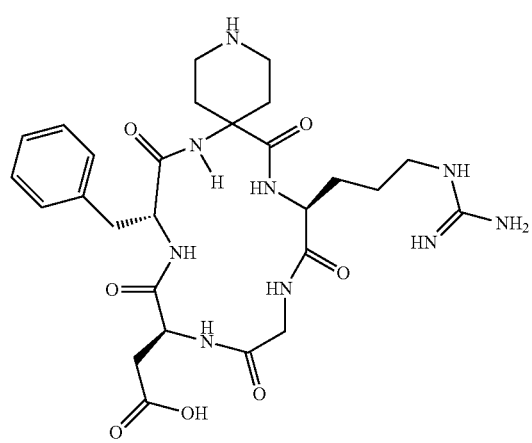

(I-1)

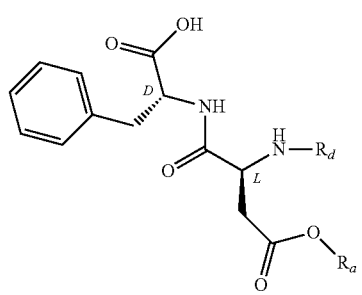

(II-1)

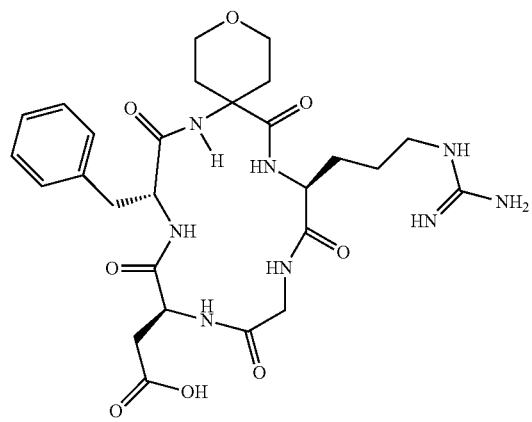

(I-2)

$R_c$—NH—$R_1$—COOH    (II-2);

wherein, Ra is alkyl, cycloalkyl, aryl, or heteroaryl;
$R_c$ is a protection group; and
$R_1$ is

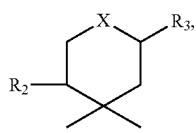

in which each of $R_2$ and $R_3$ independently is H or $C_{1-6}$ alkyl; X is O, S, $CH_2$ or N—$R_4$, in which $R_4$ is H, $C_{1-6}$ alkyl, $(CH_2CH_2O)_nH$, —C(=O)—$C_{1-10}$ alkyl, or C(=O)$(C_2H_4)_2C(=O)O(C_2H_4O)_nH$, in which n=1-3;

(B) performing a reaction between the compounds of formula (II-1) and (II-2), to obtain a compound represented by the following formula (II-3):

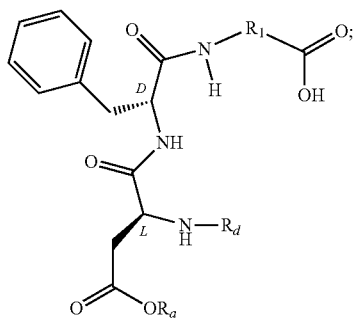

(II-3)

(C) performing a reaction between the compound of formula (II-3) and a compound represented by the following formula (II-4):

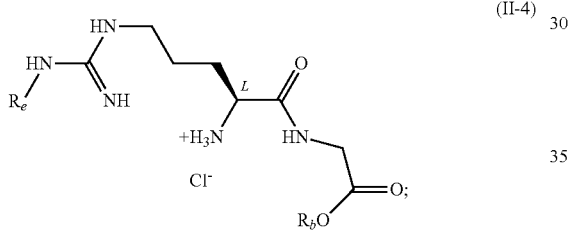

(II-4)

to obtain a compound represented by the following formula (II-5):

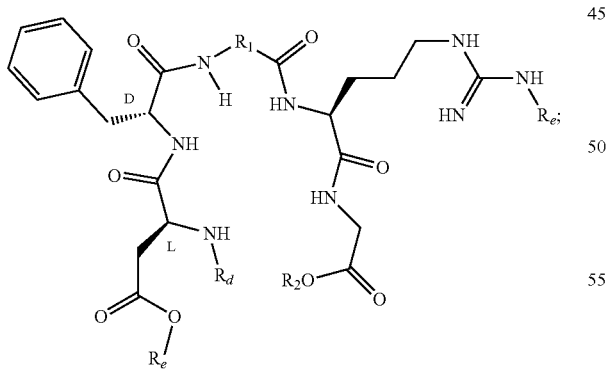

(II-5)

wherein each Rd and Re is a protection group:

(D) performing a cyclization reaction of the compound of formula (II-5) with a catalyst of formula (III);

$$M(O)_m L^1_y L^2_z \quad (III)$$

wherein M is a metal selected from the group consisting of IVB, VB, VIB and actinide groups;

$L^1$ and $L^2$ respectively is a ligand;

m and y are integers of greater than or equal to 1; and

Z is an integer of greater than or equal to zero;

to obtain a compound represented by the following formula (I):

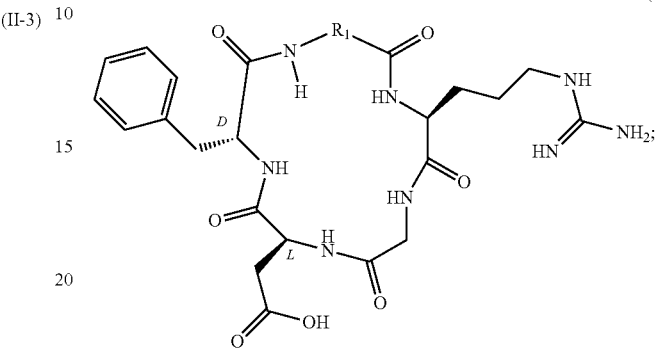

(I)

and thereby produce a compound represented by any one of the following formulas (I-1) to (I-4):

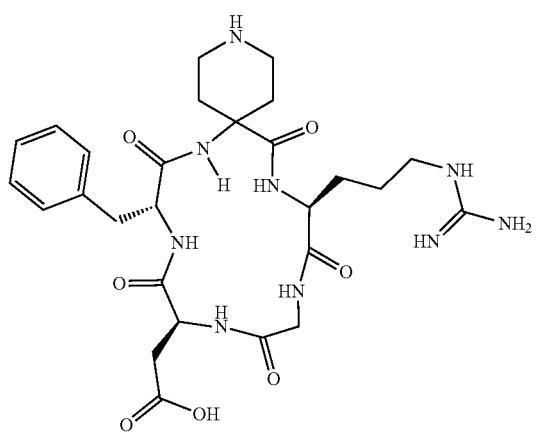

(I-1)

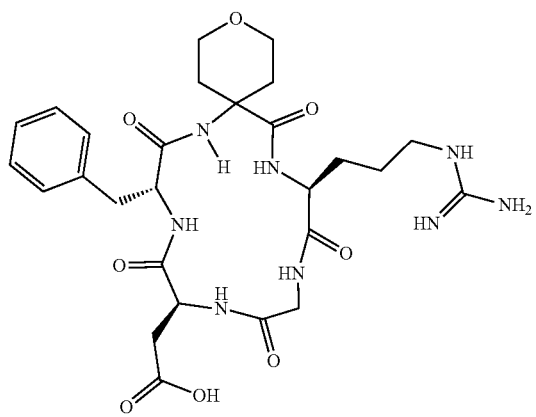

(I-2)

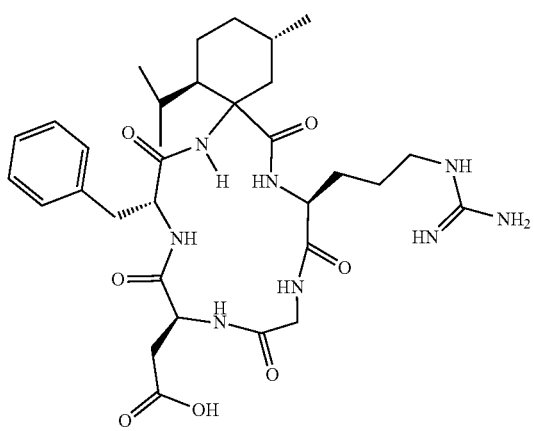
(I-3)
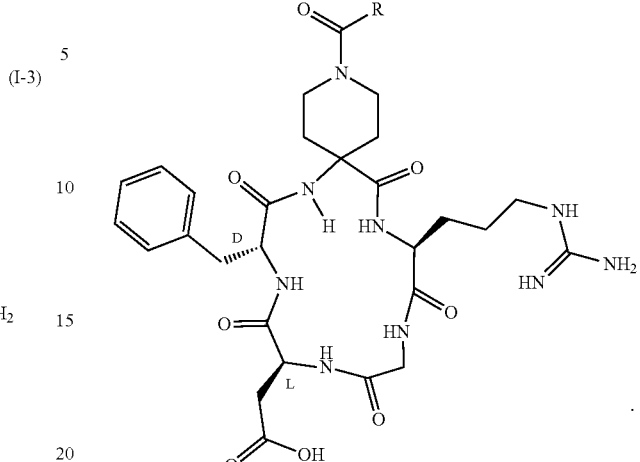
(I-4)
* * * * *